US012564618B2

(12) United States Patent
Shu et al.

(10) Patent No.:   US 12,564,618 B2
(45) Date of Patent:       Mar. 3, 2026

(54) ANTIHYPERTENSIVE PEPTIDE PROBIOTIC GOAT MILK POWDER AND PREPARATION METHOD THEREOF

(71) Applicant: SHAANXI UNIVERSITY OF SCIENCE AND TECHNOLOGY, Xi'an (CN)

(72) Inventors: Guowei Shu, Xi'an (CN); Ran Liang, Xi'an (CN); Zongcai Zhang, Xi'an (CN); Jianhao Nan, Xi'an (CN); Huan Lei, Xi'an (CN); Zhenquan Huo, Xi'an (CN); Qiannan Kong, Xi'an (CN); Chunji Dai, Xi'an (CN); Zipei Xie, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 19/208,663

(22) Filed: May 15, 2025

(65) Prior Publication Data

US 2025/0375500 A1      Dec. 11, 2025

(30) Foreign Application Priority Data

Jun. 7, 2024    (CN) .......................... 202410739016.8

(51) Int. Cl.
| | |
|---|---|
| *A61K 38/08* | (2019.01) |
| *A23C 9/123* | (2006.01) |
| *A61K 35/20* | (2006.01) |
| *A61K 35/747* | (2015.01) |
| *C12N 1/20* | (2006.01) |
| *C12N 1/205* | (2026.01) |
| *C12R 1/225* | (2006.01) |

(52) U.S. Cl.
CPC ............ *A61K 38/08* (2013.01); *A23C 9/1232* (2013.01); *A23C 9/1234* (2013.01); *A61K 35/20* (2013.01); *A61K 35/747* (2013.01); *C12N 1/205* (2021.05); *A23V 2400/175* (2023.08); *C12R 2001/225* (2021.05)

(58) Field of Classification Search
CPC ................ A23C 9/1232; A23C 9/1234; A23V 2400/175; C12R 2001/225
See application file for complete search history.

(56) References Cited

U.S. PATENT DOCUMENTS

2014/0363501 A1 * 12/2014 Chen ....................... C12N 1/205
435/252.9

OTHER PUBLICATIONS

Levine (What Are Kefir and Its Health Benefits?, WebMD, https://www.webmd.com/diet/kefir-good-for-you, Oct. 13, 2023) (Year: 2023).*

Sebastian et al. (Milk Fermentation by Lacticaseibacillus rhamnosus GG and *Streptococcus thermophilus* SY-102: Proteolytic Profile and Ace-Inhibitory Activity, Fermentation 2021, 7, 215) (Year: 2021).*
Shu et al. (Effect of Alcalase on Antioxidant and Antihypertensive Activities of Goat Milk Fermented by Lactobacillus plantarum L60 and Lactobacillus rhamnosus LR22, Acta Universitatis Cibiniensis Series E: Food Technology, vol. XXV (2021), No. 1) (Year: 2021).*
Selvaggi et al. (Major proteins in goat milk: an updated overview on genetic variability, Mol Biol Rep (2014) 41:1035-1048) (Year: 2014).*
Uniprot P00712 (goat alpha-lactalbumin, https://www.uniprot.org/uniprotkb/P00712/entry, accessed Oct. 21, 2025, sequence last updated 1988) (Year: 1988).*
Uniprot Q29477 (goat lactotransferrin, https://www.uniprot.org/uniprotkb/Q29477/entry, accessed Oct. 21, 2025, sequence last updated 1996) (Year: 1996).*
Uniprot P33048 (goat beta-casein, https://www.uniprot.org/uniprotkb/P33048/entry, accessed Oct. 21, 2025, sequence last updated 1993) (Year: 1993).*
Uniprot P18626 (goat alpha-s1-casein, https://www.uniprot.org/uniprotkb/P18626/entry, accessed Oct. 21, 2025, sequence last updated 1993) (Year: 1993).*
Uniprot P33049 (goat alpha-s2-casein, https://www.uniprot.org/uniprotkb/P33049/entry, accessed Oct. 21, 2025, sequence published 1993) (Year: 1993).*
Uniprot P02670 (goat kappa-casein, https://www.uniprot.org/uniprotkb/P02670/entry, accessed Oct. 21, 2025, sequence last updated 1992) (Year: 1992).*
Uniprot P02756 (goat beta-lactoglobulin, https://www.uniprot.org/uniprotkb/P02756/entry, accessed Oct. 21, 2025, sequence last updated 1992) (Year: 1992).*
CNIPA, Notification of First Office Action for CN202410739016.8, Nov. 27, 2024.
Shaanxi University of Science & Technology (Applicant), Replacement claims (allowed) of CN202410739016.8, Nov. 28, 2024.
CNIPA, Notification to grant patent right for invention in CN202410739016.8, Mar. 3, 2025.

* cited by examiner

*Primary Examiner* — Louise W Humphrey
*Assistant Examiner* — Alexander M Duryee

(57)                   ABSTRACT

An antihypertensive peptide probiotic goat milk powder and a preparation method thereof are provided. Goat milk is used as a raw material, the goat milk is sterilized and then cooled, and the screened probiotic bacteria for fermenting goat milk to produce antihypertensive peptides, namely *Lacticaseibacillus rhamnosus* KD5 (which is preserved in CCTCC on Sep. 7, 2023, with a preservation number of CCTCC NO: M20231641), is added and stirred evenly, and then fermented at a constant temperature. After the fermentation is completed, probiotic fermented goat milk containing antihypertensive peptides is obtained. After mixing the probiotic fermented goat milk evenly with or without nutritional fortifiers for middle-aged and elderly people, it is subjected to vacuum low-temperature spray-drying to obtain antihypertensive peptide probiotic goat milk powder, which has a high ACE inhibition rate and can be used to assist consumers in lowering blood pressure.

1 Claim, 24 Drawing Sheets

Specification includes a Sequence Listing.

ANTIHYPERTENSIVE PEPTIDE PROBIOTIC GOAT MILK POWDER AND PREPARATION METHOD THEREOF

CROSS-REFERENCE TO RELATED APPLICATION

This application claims priority to Chinese Patent Application No. 202410739016.8, filed on Jun. 7, 2024, which is herein incorporated by reference in its entirety.

TECHNICAL FIELD

The disclosure relates to the technical field of fermentation engineering, and more particularly to an antihypertensive peptide probiotic goat milk powder obtained by fermenting goat milk with *Lacticaseibacillus rhamnosus* KD5 and spray-drying at a low-temperature, and a preparation method thereof.

STATEMENT REGARDING SEQUENCE LISTING

The sequence listing associated with this application is provided in text format in lieu of a paper copy and is hereby incorporated by reference into the specification. The name of the XML file containing the sequence listing is 25009MYZ-USP1-SL.xml. The XML file is 14,844 bytes; is created on Apr. 16, 2025; and is being submitted electronically via patent center.

BACKGROUND

Currently, there are six major categories of drugs for treating hypertension, including: diuretics, calcium channel blockers, angiotensin II receptor antagonists (ARBs), angiotensin converting enzyme inhibitors (ACEIs), α-adrenergic antagonists and β-blockers.

ACEIs offer significant advantages for hypertensive patients, including effective blood pressure reduction, target organ protection, and prevention of cardiovascular endpoint events. Additionally, ACEIs do not adversely affect glucose or lipid metabolism. Due to these advantages, ACEIs have become one of the fastest-growing classes of antihypertensive drugs today. Commonly used ACEI drugs include captopril, enalapril, benazepril, ramipril, perindopril, alacepril and lisinopril. However, these synthetic ACEIs can cause many adverse reactions, and the most common of which is persistent dry cough. In addition, they can also cause hypotension, rash and taste disorders.

Since the synthetic ACEIs have many side effects and long-term use will produce multiple side effects, food-derived angiotensin-converting enzyme (ACE) inhibitory peptides have attracted people's attention. The ACE inhibitory peptides are polypeptides that can reduce the activity of ACE. Although there are differences in amino acid sequences and peptide lengths of the ACE inhibitory peptides, they all can lower blood pressure, leading to their classification as antihypertensive peptides. Compared with chemically synthesized antihypertensive drugs, the food-derived ACE inhibitory peptides have extremely high safety. Studies have shown that the ACE inhibitory peptides have a better antihypertensive effect on the hypertension patients, but have no effect on people with normal blood pressure and no side effects. This selective antihypertensive effect is not available in ordinary chemically synthesized antihypertensive drugs. Therefore, various preparation studies on food-derived ACE inhibitory peptides have been carried out in the industry.

Goat milk products mainly include infant formula goat milk powder, bulk goat milk powder and dry-mixed formulated goat milk powder. There are few product varieties, serious homogeneity and fierce competition. Therefore, it is necessary to develop functional goat milk powder.

SUMMARY

In order to solve the problems in the related art, the disclosure provides an antihypertensive peptide probiotic goat milk powder and a preparation method thereof. Fresh goat milk or reconstituted goat milk are used as a raw material, the goat milk is fermented with *Lacticaseibacillus rhamnosus* KD5 to decompose protein in the goat milk into antihypertensive peptides, the antihypertensive peptides are separated and purified and amino acid sequences of the antihypertensive peptides are identified to determine positions of the antihypertensive peptides in the protein of the goat milk. At the same time, the fermented goat milk is spray-dried at low-temperature in vacuum to obtain the antihypertensive peptide probiotic goat milk powder.

In order to achieve the above purposes, the disclosure provides the following technical solutions: a *Lacticaseibacillus rhamnosus* KD5 is provided, preserved at China Center for Type Culture Collection (CCTCC) with a preservation number of CCTCC NO: M20231641.

In an embodiment, the *Lacticaseibacillus rhamnosus* KD5 is non-hemolytic and sensitive to ciprofloxacin, chloramphenicol, clindamycin, ceftriaxone, gentamicin, penicillin, and tetracycline; the *Lacticaseibacillus rhamnosus* KD5 has a hydrophobicity of 52.28% in xylene, a self-aggregation rate of 58.86%, and a co-aggregation rate of more than 40% for *Escherichia coli* and *Staphylococcus aureus*.

The disclosure further provides an antihypertensive dairy product, and the above *Lacticaseibacillus rhamnosus* KD5 is used to ferment goat milk to obtain the antihypertensive dairy product containing antihypertensive peptides.

In an embodiment, amino acid sequences of the antihypertensive peptides include:

FLDDD (SEQ ID NO: 1), SLPEW (SEQ ID NO: 2), IMGVPK (SEQ ID NO: 3), FAWPQ (SEQ ID NO: 4), LHLPLP (SEQ ID NO: 5), MPIQAF (SEQ ID NO: 6), EPINIF (SEQ ID NO: 7), LPQNILP (SEQ ID NO: 8), LPYPYY (SEQ ID NO: 9), TPVVVPPF (SEQ ID NO: 10), LAFNPTQL (SEQ ID NO: 11), KNRLNFL (SEQ ID NO: 12), FVVAPFPE (SEQ ID NO: 13), LTLTDVEK (SEQ ID NO: 14), KYIPIQY (SEQ ID NO: 15) and VPPFLQPE (SEQ ID NO: 16).

The disclosure further provides an antihypertensive peptide probiotic goat milk, which is obtained by fermenting goat milk with the above *Lacticaseibacillus rhamnosus* KD5. An inoculation amount of the *Lacticaseibacillus rhamnosus* KD5 is in a range of 0.01% to 0.05%, an angiotensin-converting enzyme (ACE) inhibition rate of the antihypertensive peptide probiotic goat milk is in a range of 65.90% to 83.25%, and a power of hydrogen (pH) of the antihypertensive peptide probiotic goat milk is in a range of 3.56 to 4.59.

The disclosure further provides a preparation method of an antihypertensive peptide probiotic goat milk, including:

S1, adding 0.01% to 0.05% of lyophilized powder of *Lacticaseibacillus rhamnosus* KD5 into sterilized and cooled goat milk to obtain a mixture; and S2, fermenting the mixture at a constant temperature of 34 Celsius degrees (° C.) to 40° C. for 22 hours (h) to 26 h, to obtain the antihypertensive peptide probiotic fermented goat milk.

In an embodiment, the antihypertensive peptide probiotic goat milk is added with a nutritional fortifier for middle-aged and elderly people, and the nutritional fortifier is one or more selected from the group consisting of phosphati-dylserine, acetylneuraminic acid, and prebiotics.

The disclosure further provides antihypertensive peptide probiotic goat milk powder, which is prepared by fermenting goat milk with the above *Lacticaseibacillus rhamnosus* KD5 and spray-drying the fermented goat milk. An inoculation amount of the *Lacticaseibacillus rhamnosus* KD5 is in a range of 0.01% to 0.05%, a half inhibitory concentration ($IC_{50}$) value of ACE inhibition by the antihypertensive peptide probiotic goat milk powder is in a range of 0.0545 grams per milliliter (g/mL) to 0.0840 g/mL, a survival rate of probiotic is in a range of 53.19% to 83.58%, and a viable count of probiotics in the antihypertensive peptide probiotic goat milk powder is in a range of $4.41 \times 10^8$ colony-forming units per gram (CFU/g) to $6.94 \times 10^8$ CFU/g.

The disclosure further provides a preparation method of antihypertensive peptide probiotic goat milk powder, including:

S1, adding 0.01% to 0.05% of lyophilized powder of *Lacticaseibacillus rhamnosus* KD5 into sterilized and cooled goat milk to obtain a mixture;

S2, fermenting the mixture at a constant temperature of 34° C. to 40° C. for 22 h to 26 h, to obtain the antihypertensive peptide probiotic goat milk; and S3, vacuum low-temperature spray-drying the antihyper-tensive peptide probiotic fermented goat milk to obtain the antihypertensive peptide probiotic goat milk pow-der.

In an embodiment, conditions of the spray-drying in vacuum include: 0.03 megapascals (MPa) to 0.036 MPa of vacuum negative pressure, and 65° C. to 75° C. of an inlet air temperature.

Compared with the related art, the disclosure at least includes the following beneficial effects.

The disclosure provides *Lacticaseibacillus rhamnosus* KD5, which was preserved in the CCTCC on Sep. 7, 2023, with a preservation number of CCTCC NO: M20231641. The *Lacticaseibacillus rhamnosus* KD5 has good hydropho-bic properties, and it is speculated that it has good intestinal adhesion ability. The *Lacticaseibacillus rhamnosus* KD5 is sensitive to 7 antibiotics such as chloramphenicol, clin-damycin, ceftriaxone, gentamicin, and tetracycline, thus it is not easy to develop drug resistance and has good safety. The *Lacticaseibacillus rhamnosus* KD5 has strong self-aggrega-tion and coaggregation abilities, and shows higher acid and bile resistance than *Lactiplantibacillus plantarum* 7830 and *Lacticaseibacillus rhamnosus* L20. In addition, the *Lactica-seibacillus rhamnosus* KD5 is derived from kefir grains, which has the advantages of being natural, green, and safe.

The disclosure provides an antihypertensive peptide pro-biotic goat milk. The *Lacticaseibacillus rhamnosus* KD5 is used to ferment the goat milk, thereby enriching the types of goat milk products. The fermented goat milk has a high ACE inhibition rate and can be used by consumers to assist in lowering blood pressure.

The disclosure provides an antihypertensive peptide pro-biotic goat milk powder. The production process adopts spray drying at low-temperature in vacuum. The viable count of probiotics of the prepared antihypertensive peptide probiotic goat milk powder is significantly higher than that of probiotics of goat milk powder prepared by high-tem-perature spray-drying, thereby avoiding the problems of low survival rate of the probiotic and low viable count of the probiotics caused by conventional high-temperature spray-drying.

DETAILED DESCRIPTION OF EMBODIMENTS

Figure 1A:
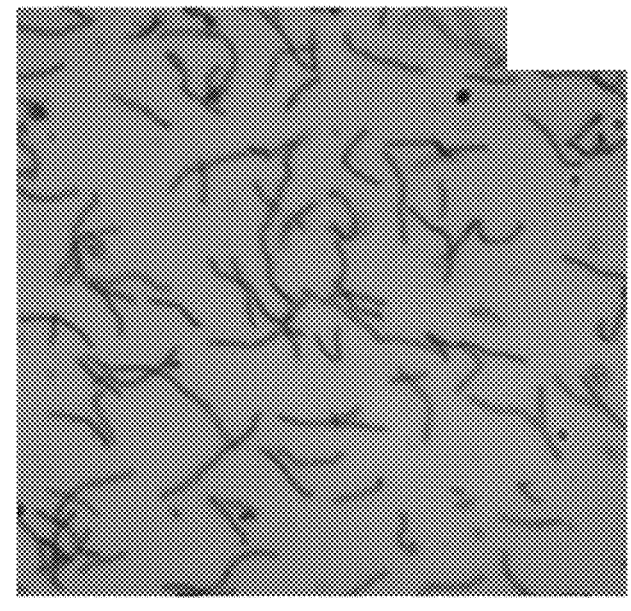
FIG. 1A illustrates a schematic diagram of a mycelial morphology of *Lacticaseibacillus rhamnosus* KD5.

The disclosure is further described in conjunction with drawings and embodiments below.

The disclosure provides an antihypertensive peptide probiotic goat milk powder, the probiotic is *Lacticaseibacillus rhamnosus* KD5, which is classified and named *Lacticaseibacillus rhamnosus*, a preservation number is CCTCC NO: M20231641, a preservation time is Sep. 7, 2023, a preservation unit is CCTCC, with an address of Wuhan University, No. 299, Bayi Road, Wuchang District, Wuhan City, Hubei Province, and a zip code of 430072.

The disclosure provides a preparation method of antihypertensive peptide probiotic goat milk powder. Fresh goat milk or reconstituted goat milk are used as a raw material, the goat milk is fermented with *Lacticaseibacillus rhamnosus* KD5 to decompose protein in the goat milk into antihypertensive peptides, the antihypertensive peptides are separated and purified and amino acid sequences of the antihypertensive peptides are identified to determine positions of the antihypertensive peptides in the protein of the goat milk. At the same time, the fermented goat milk is spray-dried at low-temperature in vacuum to obtain the antihypertensive peptide probiotic goat milk powder.

Embodiment 1 Isolation and Identification of
*Lacticaseibacillus rhamnosus* KD5

1. Isolation of *Lacticaseibacillus rhamnosus* KD5

A certain amount of whole goat milk powder is weighed, and added with distilled water according to a ratio of 1:7 (weight/volume abbreviated as w/v) to make reconstituted goat milk. The reconstituted goat milk is sterilized at 115° C. for 10 minutes (min) to obtain sterilized reconstituted goat milk, kefir grains (purchased from TAOBAO® Store, Xizang Linzhi Natural Saussurea) is added into the sterilized reconstituted goat milk, and the sterilized reconstituted goat milk added with the kefir grains is fermented at a constant temperature of 25° C. for 22 h to obtain goat milk kefir. After fermentation is completed, the goat milk kefir grains are filtered out from the goat milk kefir. The goat milk kefir grains are washed with sterilized saline to activate once, the operation (i.e., washed with sterilized saline) is repeated and continue to activate 4 times. The obtained goat milk kefir grains after activating 4 times are crushed and stirred evenly to obtain an even mixture. 5 milliliters (mL) of the even mixture is added into 45 mL of sterile saline to mix evenly, to prepare a diluent. 1 mL of the diluent is added into 9 mL of sterile saline and shake vigorously to make bacteria evenly distributed. The above operation steps are repeated until a dilution factor reaches $10^{-6}$ to $10^{-8}$. 0.1 mL of the diluent is absorbed and coated on a De Man, Rogosa, and Sharpe (MRS) agar plate (ingredients include 10 grams (g) peptone, 5 g beef powder, 4 g yeast powder, 2 g potassium dihydrogen phosphate, 2 g ammonium citrate, 5 g sodium acetate, 20 g glucose, 1 mL polysorbate 80 (also referred to as TWEEN 80), 0.2 g magnesium sulfate, 0.05 g manganese sulfate, 15 g agar, and 1000 ml distilled water). The MRS agar plate is cultured at 37° C. for 48 h until obvious single colonies are formed. A plate with 30 to 80 single colonies is selected from the culture medium, typical colonies are picked, and multiple streaking purifications are performed on the MRS solid plate culture medium until the colony morphology on the entire plate is consistent. A single colony is selected and inoculated into MRS broth (10 g peptone, 5 g beef powder, 4 g yeast powder, 2 g potassium dihydrogen phosphate, 2 g ammonium citrate, 5 g sodium acetate, 20 g glucose, 1 mL polysorbate 80, 0.2 g magnesium sulfate, 0.05 g manganese sulfate, and 1000 ml distilled water) and then cultured at 37° C. for 24 h. Then, aseptically take 0.1 mL of the shaken culture solution into a lyophilization tube in an ultra-clean workbench, 0.1 mL of sterile skim milk is added into the lyophilization tube to mix evenly, followed by freeze-dried, and stored in a refrigerator.

2. Identification of *Lacticaseibacillus rhamnosus* KD5

2.1. Colony and Mycelial Morphology

Figure 1B:
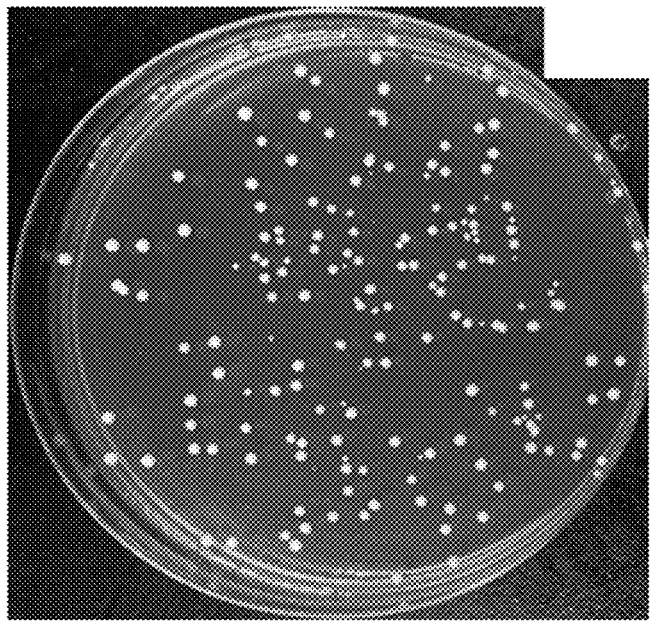
FIG. 1B illustrates a schematic diagram of a colony morphology of the *Lacticaseibacillus rhamnosus* KD5.

After the *Lacticaseibacillus rhamnosus* KD5 is cultured in the MRS agar culture medium for 48 h, the *Lacticaseibacillus rhamnosus* KD5 forms obvious colonies on the MRS agar culture medium, which are round, with neat edges, milky white, moist and smooth surfaces, and no pigment is produced, as shown in FIG. 1B. A mycelial morphology of the *Lacticaseibacillus rhamnosus* KD5 after staining with toluidine blue is long rod-shaped, and some of the bacteria are bent, as shown in FIG. 1A.

2.2 Strain Identification 2.2.1 Identification by a Fully Automatic Microbial Mass Spectrometer (VITEK MS, BioMérieux, France)

Figure 2:
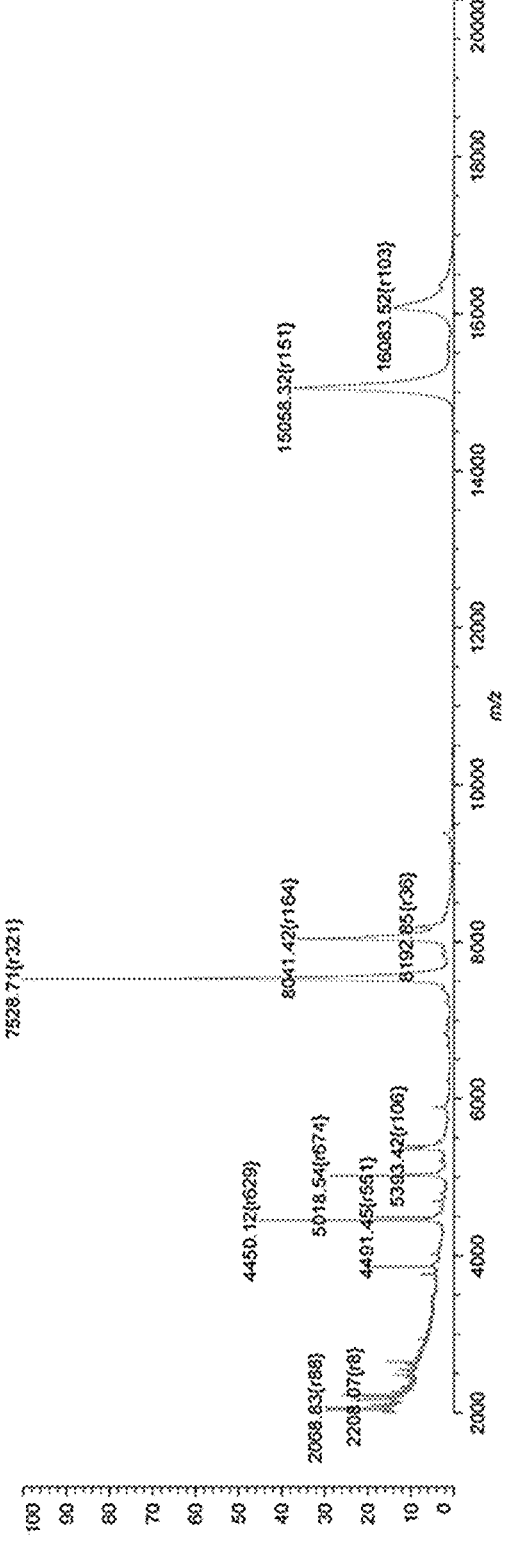
FIG. 2 illustrates a matrix-assisted laser desorption/ion-ization time-of-flight mass spectrometry (MALDI-TOF-MS) identification diagram of the *Lacticaseibacillus rham-nosus* KD5.

*Lactobacillus* is inoculated on a Columbia blood agar plate and cultured at 37° C. for 24 h. Pinpoint-sized colonies are evenly coated on a target plate, and 1 microliter (μL) of matrix solution is added on the target plate to mix evenly. After drying, a sample is loaded onto the fully automatic microbial mass spectrometer for sample analysis and compared with a VITEK-MS mass spectrometer research library. A name of the strain is determined based on the characteristic peaks. The MALDI-TOF-MS identification diagram is shown in FIG. 2.

2.2.2 Identification by a Fully Automatic Microbial Identification Instrument (VITEK 2, BioMérieux, France)

A *Lactobacillus* colony is taken and added with 3 mL of 0.45% saline to obtain a bacterial suspension with a McFarland turbidity of 0.5. A gram-positive bacilli identification card is inserted into the bacterial suspension, and then placed on a microbial identification instrument. After the bacterial suspension is put on the machine, biochemical reaction results are obtained. According to the biochemical reaction results, a microbial identification database, such as ASE8.01 database, is compared to identify and determine the name of the bacterial species. The biochemical reaction identification results are shown in Table 1.

TABLE 1

| Biochemical reaction identification results of *Lacticaseibacillus rhamnosus* KD5 | | | | | | | | |
|---|---|---|---|---|---|---|---|---|
| Hole number | Biochemical reaction | Result | Hole number | Biochemical reaction | Result | Hole number | Biochemical reaction | Result |
| 2 | AMY | + | 3 | PIPLC | − | 5 | dXYL | − |
| 8 | ADH1 | − | 9 | BGAL | − | 11 | AGLU | − |

TABLE 1-continued

Biochemical reaction identification results of *Lacticaseibacillus rhamnosus* KD5

| Hole number | Biochemical reaction | Result | Hole number | Biochemical reaction | Result | Hole number | Biochemical reaction | Result |
|---|---|---|---|---|---|---|---|---|
| 13 | APPA | + | 14 | CDEX | + | 15 | AspA | − |
| 16 | BGAR | − | 17 | AMAN | − | 19 | PHOS | − |
| 20 | LeuA | + | 23 | ProA | + | 24 | BGURr | − |
| 25 | AGAL | − | 26 | PyrA | + | 27 | BGUR | − |
| 28 | AlaA | + | 29 | TyrA | + | 30 | dSOR | + |
| 31 | URE | − | 32 | POLYB | − | 37 | dGAL | + |
| 38 | dRIB | + | 39 | ILATk | − | 42 | LAC | + |
| 44 | NAG | + | 45 | dMAL | + | 46 | BACI | + |
| 47 | NOVO | + | 50 | NC6.5 | + | 52 | dMAN | + |
| 53 | dMNE | + | 54 | MBdG | + | 56 | PUL | + |
| 57 | dRAF | − | 58 | O129R | + | 59 | SAL | + |
| 60 | SAC | + | 62 | dTRE | + | 63 | ADH2s | − |
| 64 | OPTO | + | | | | | | |

Note:
+ represents a positive biochemical reaction; and − represents a negative biochemical reaction.

Mass spectral characteristic peaks of KD10 and KD5 are analyzed by using a microbial identification software (such as Launch pad software of the VITEK-MS mass spectrometer research library (research use only abbreviated as RUO)). FIG. 2 illustrates a MALDI-TOF-MS identification diagram of *Lacticaseibacillus rhamnosus* KD5. The mass spectral peaks mass-to-charge ratio (m/z) 2068.83, 2208.07, 4450.12, 4491.45, 5018.64, 5393.42, 7528.71, 8041.42, 8192.85, 15058.32, and 16083.52 are characteristic peaks of *Lacticaseibacillus rhamnosus*, and the identification results are all in line with the credibility of more than 99%. Table 1 is the biochemical reaction results of *Lacticaseibacillus rhamnosus* KD5. After comparison with the AES8.01 database, KD5 is *Lacticaseibacillus rhamnosus*, and the identification results are all in line with the credibility of more than 99%. In summary, the two methods identify strain KD5 as *Lacticaseibacillus rhamnosus*, and it is preserved in the CCTCC on Sep. 7, 2023, with the preservation number of CCTCC NO: M20231641.

Embodiment 2 Test of Probiotic Properties of
*Lacticaseibacillus rhamnosus* KD5

1. Hemolytic Assay

Activated *Lacticaseibacillus rhamnosus* KD5, activated *Lactiplantibacillus plantarum* 7830, activated *Lacticaseibacillus rhamnosus* L20 and hemolytic *Escherichia coli* are respectively coated on surfaces of Columbia blood agar plates added with 5% sterile defibrinated goat blood and cultured at 37° C. for 48 h. The hemolytic activity of the probiotics is evaluated based on different halos. The results are shown in FIG. 3.

Figure 3:
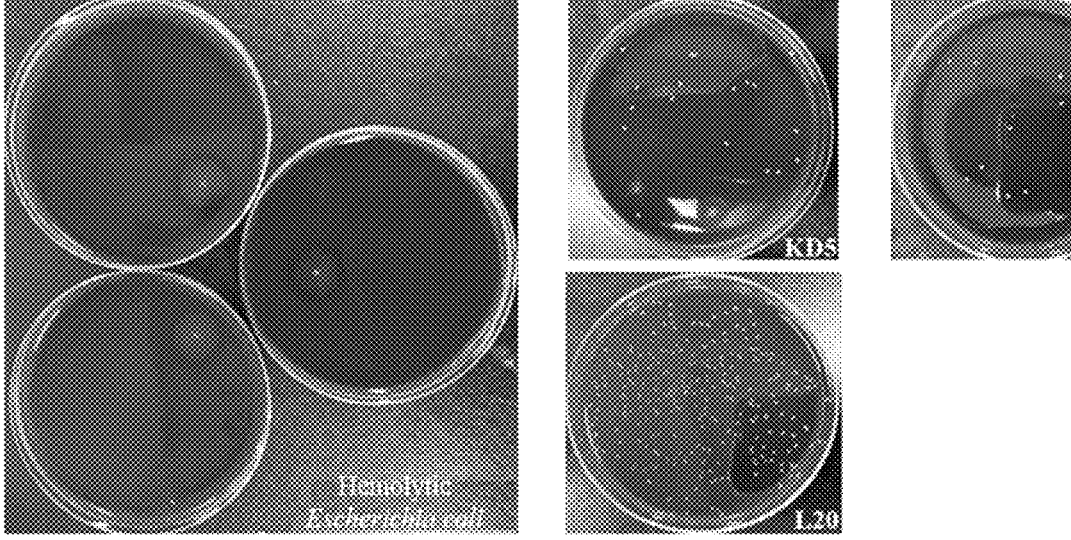
FIG. 3 illustrates a schematic diagram of hemolysis of the *Lacticaseibacillus rhamnosus* KD5, *Lactiplantibacillus plantarum* 7830, *Lacticaseibacillus rhamnosus* L20 and *Escherichia coli*.

It can be seen from FIG. 3, obvious transparent halos are observed on the Columbia blood agar plate inoculated with the hemolytic *Escherichia coli*, which is β-hemolysis, while no hemolysis is observed on the Columbia blood agar plates inoculated with the *Lacticaseibacillus rhamnosus* KD5, the *Lactiplantibacillus plantarum* 7830, and the *Lacticaseibacillus rhamnosus* L20, indicating that these three strains are non-hemolytic, that is, they are all safe strains. The lack of hemolysis ensures the safety of the strains and is used as one of the screening criteria for probiotic strains.

2. Antibiotic Sensitivity Determination

A total of 9 antibiotics, including chloramphenicol (C, 30 micrograms abbreviated as μg), clindamycin (CC, 2 μg), ciprofloxacin (CIP, 5 μg), ceftriaxone (CTR, 30 μg), gentamicin (GM, 10 μg), penicillin (PEN, 10U), streptomycin (S, 10 μg), tetracycline (TET, 30 μg), and vancomycin (VAN, 30 μg), are selected to evaluate the antibiotic resistance of the *Lacticaseibacillus rhamnosus* KD5, the *Lactiplantibacillus plantarum* 7830, and the *Lacticaseibacillus rhamnosus* L20. The results are shown in FIG. 4.

Figure 4:
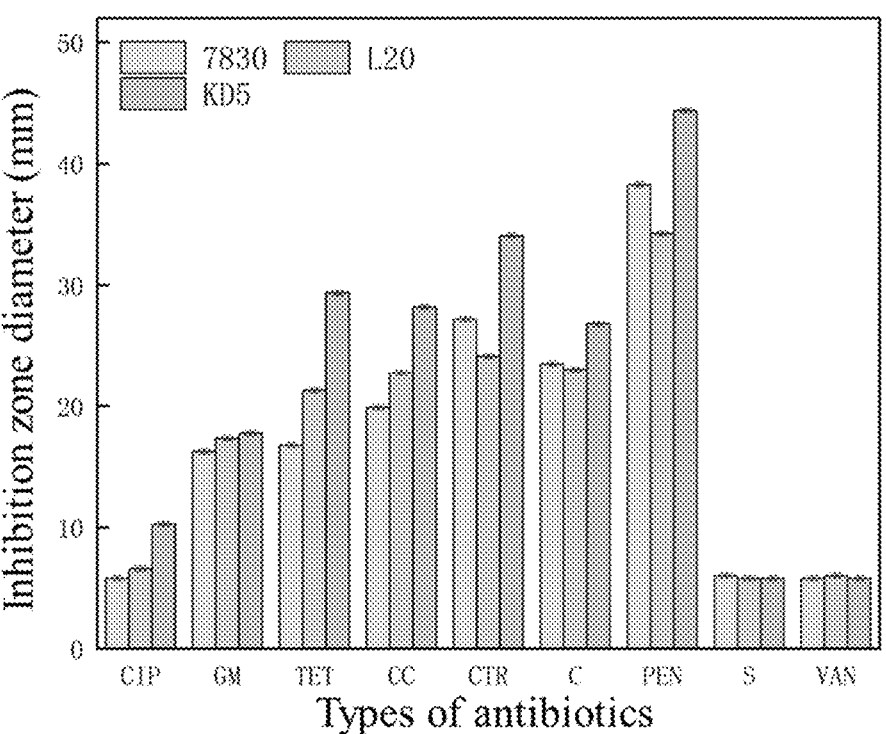
FIG. 4 illustrates a schematic diagram of sensitivity of the *Lacticaseibacillus rhamnosus* KD5, the *Lactiplantibacillus plantarum* 7830, and the *Lacticaseibacillus rhamnosus* L20 to antibiotics.

It can be seen from FIG. 4, the three probiotics are generally sensitive to penicillin (PEN), with an inhibition zone ranging from 34.26 millimeters (mm) to 44.38 mm. The *Lactiplantibacillus plantarum* 7830 and the *Lacticaseibacillus rhamnosus* L20 are resistant to ciprofloxacin (CIP), streptomycin(S) and vancomycin (VAN), while the *Lacticaseibacillus rhamnosus* KD5 is sensitive to ciprofloxacin (CIP) with an inhibition zone of 10.71 mm. Inhibition zones of the *Lacticaseibacillus rhamnosus* KD5 to tetracycline (TET) and clindamycin (CC) are 28.71 mm and 26.31 mm, respectively. In summary, the *Lacticaseibacillus rhamnosus* KD5 is sensitive to seven antibiotics, including penicillin (PEN), ciprofloxacin (CIP), chloramphenicol (C), clindamycin (CC), ceftriaxone (CTR), gentamicin (GM), and tetracycline (TET), is not prone to drug resistance, and has high safety.

3. Tolerance to Simulated Gastric Fluid and Simulated Intestinal Fluid

Simulated gastric fluid is prepared as follows. 4 g of pepsin is accurately weighed and dissolved in a sterilized phosphate-buffered saline (PBS) solution, a pH of the PBS solution containing pepsin is adjusted to 2.0 with 1 mole per liter (mol/L) hydrochloric acid (HCl) solution, and then make up to 100 mL with 0.1 mol/L HCl solution. After filtering and sterilizing, the simulated gastric fluid is stored at 4° C. for later use.

Simulated intestinal fluid is prepared as follows. 0.2 g trypsin and 1.8 g ox bile salt are accurately weighed and dissolved in a sterilized PBS solution, a pH of the PBS solution containing trypsin and ox bile salt is adjusted to 8.0 with 1 mol/L sodium hydroxide (NaOH) solution, and then make up to 100 mL with 0.1 mol/L NaOH solution. After filtering and sterilizing, the simulated intestinal fluid is stored at 4° C. for later use.

3.1 Simulated Gastric Fluid Test

Figures 5A, 5B:
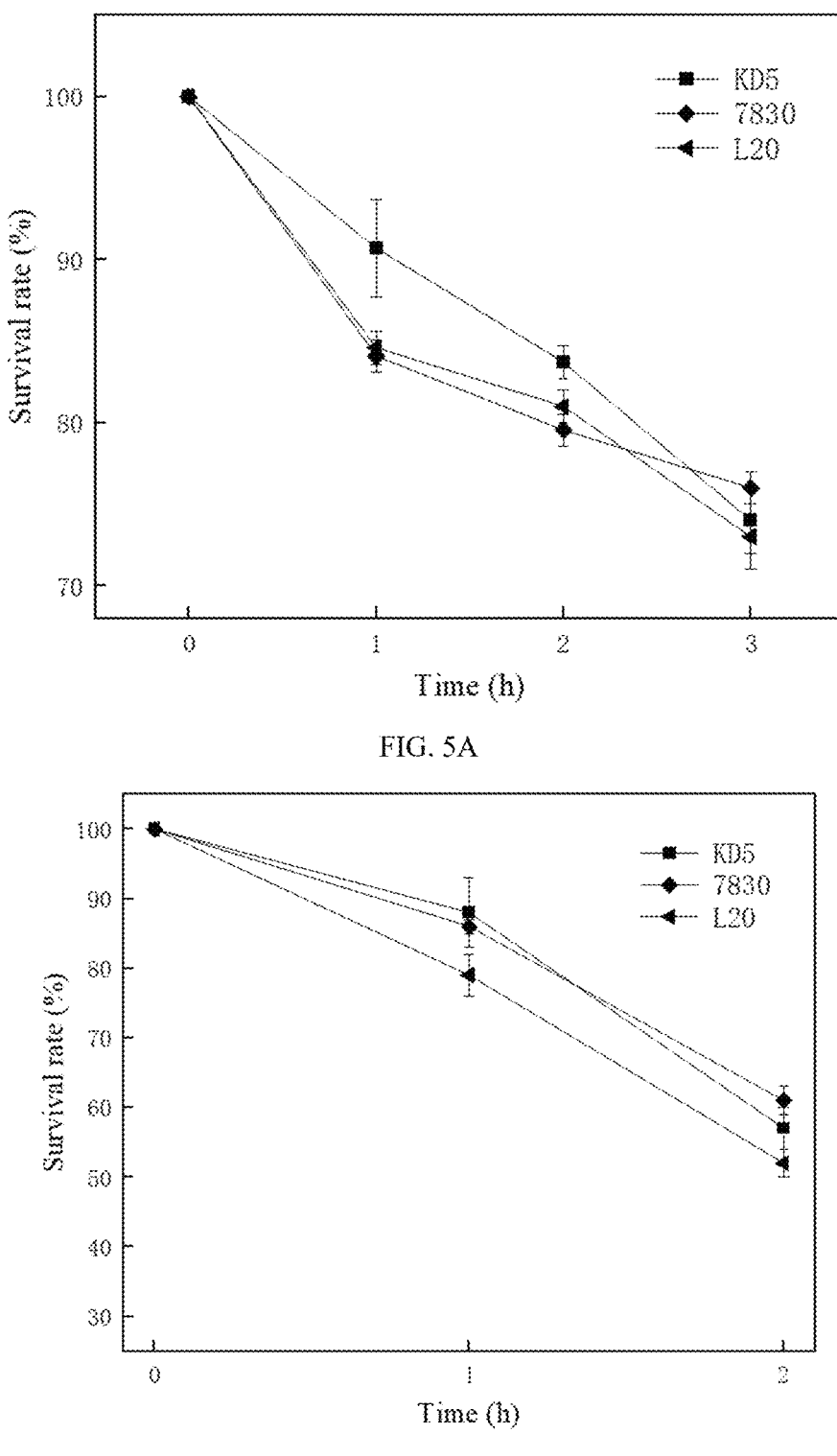
FIG. 5A illustrates a schematic diagram of tolerance of the *Lacticaseibacillus rhamnosus* KD5, the *Lactiplantibacillus plantarum* 7830, and the *Lacticaseibacillus rhamnosus* L20 to simulated gastric fluid.
FIG. 5B illustrates a schematic diagram of tolerance of the *Lacticaseibacillus rhamnosus* KD5, the *Lactiplantibacillus plantarum* 7830, and the *Lacticaseibacillus rhamnosus* L20 to simulated intestinal fluid.

The *Lacticaseibacillus rhamnosus* KD5, the *Lactiplantibacillus plantarum* 7830, and the *Lacticaseibacillus rhamnosus* L20 are inoculated into the prepared artificial gastric fluid (i.e., the simulated gastric fluid) at an inoculum volume of 5%, and placed in a shaker at 37° C. and 210 revolutions per minute (r/min) for 3 h. The treated liquid is collected at four time periods of 0 h, 1 h, 2 h, and 3 h, and viable counts are determined. The results are shown in FIG. 5A.

3.2 Simulated Intestinal Fluid Test

The probiotic liquid treated in the simulated gastric fluid for 3 h is centrifuged and washed twice to obtain probiotic sludge. The probiotic sludge is collected and inoculated into the prepared artificial intestinal fluid (i.e., the simulated intestinal fluid). The treatment method is the same as that of gastric fluid. The results are shown in FIG. 5B.

It can be seen from FIG. 5, a survival rate of each strain in the simulated gastric fluid and the simulated intestinal fluid decreased with the extension of the treatment time, and the survival rate is in a range of 13.88% to 38.36%. The survival rate of the *Lactiplantibacillus* plantarum 7830 is the highest, and the final survival rate is 38.36%. The survival rate of the *Lacticaseibacillus rhamnosus* L20 is the lowest, and the final survival rate is only 13.88%. In the 3 h of gastric fluid treatment, the decrease in survival rate is significantly higher than that in intestinal fluid. In the first 3 h of gastric fluid treatment, the survival rate ranking of the three probiotics is: *Lactiplantibacillus* plantarum 7830>*Lacticaseibacillus* rhamnosus KD5>*Lacticaseibacillus rhamnosus* L20. In the last 2 h of intestinal fluid treatment of the three probiotics, the survival rate of the *Lacticaseibacillus rhamnosus* KD5 is better than that of the *Lactiplantibacillus* plantarum 7830 and the *Lacticaseibacillus rhamnosus* L20. It can be seen that the survival rate of probiotics in intestinal fluid is greatly affected by the early gastric fluid treatment, and the decrease in survival rate in the later intestinal fluid treatment gradually slows down.

4. Hydrophobicity Determination

Figure 6:
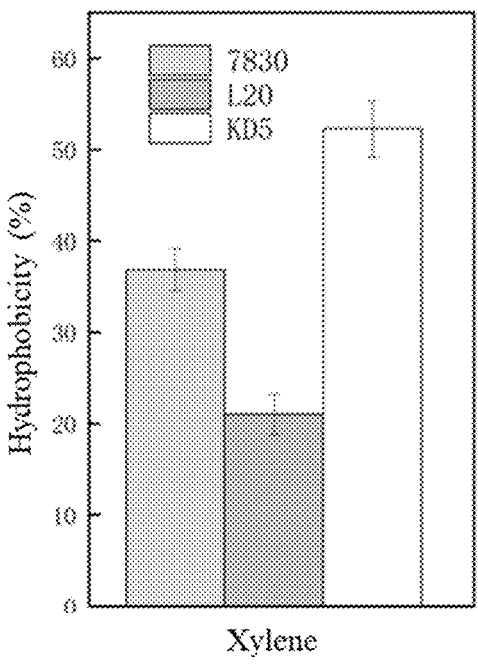
FIG. 6 illustrates a schematic diagram of hydrophobicity of the *Lacticaseibacillus rhamnosus* KD5, the *Lactiplanti-bacillus plantarum* 7830, and the *Lacticaseibacillus rham-nosus* L20.

The hydrophobicity of the *Lacticaseibacillus rhamnosus* KD5, the *Lactiplantibacillus* plantarum 7830, and the *Lacticaseibacillus rhamnosus* L20 is determined according to the following formula, and the results are shown in FIG. 6:

$$\text{Hydrophobicity } H(\%) = \frac{A - A_0}{A} \times 100$$

where A represents absorbance before mixing with hydrophobic solvent; and $A_0$ represents absorbance after mixing with hydrophobic solvent.

It can be seen from FIG. 6, the hydrophobicity of the three probiotics in xylene is in a range of 21% to 52.28%. Among them, the *Lacticaseibacillus rhamnosus* KD5 and the *Lactiplantibacillus* plantarum 7830 have higher hydrophobicity (P<0.05), which are 52.28% and 36.86% respectively. The surface hydrophobicity of bacteria mainly depends on the non-polar groups on the surface of bacteria, which may be related to structures such as surface proteins, pili, lipoteichoic acid and capsule. The hydrophobicity of probiotic directly reflects its adhesion ability to intestinal epithelial cells. In the disclosure, the *Lacticaseibacillus rhamnosus* KD5 shows good hydrophobicity, and it is speculated that it has good intestinal adhesion ability.

5. Self-Aggregation and Coaggregation Assay 5.1 A formula for calculating a self-aggregation rate of each of the *Lacticaseibacillus rhamnosus* KD5, the *Lactiplantibacillus* plantarum 7830, and the *Lacticaseibacillus rhamnosus* L20 is as follows:

$$\text{Self-aggregation rate }(\%) = \frac{A_0 - A_t}{A_0} \times 100$$

where $A_0$ represents an optical density at 600 nanometers $(OD_{600\ nm})$ of the probiotic suspension at 0 h; and $A_t$ represents an $OD_{600\ nm}$ value measured at different time points after standing.

5.2 Standard pathogenic strains used are *Escherichia coli* DC and *Staphylococcus aureus* JP stored frozen in the laboratory. A formula for calculating a coaggregation rate of each of the *Lacticaseibacillus rhamnosus* KD5, the *Lactiplantibacillus* plantarum 7830, and the *Lacticaseibacillus rhamnosus* L20 is as follows:

$$\text{Coaggregation rate }(\%) = \frac{A_{pro} + A_{pat} - A_{mix}}{A_{pro} + A_{pat}} \times 100$$

where $A_{pro}+A_{pat}$ represents an $OD_{600\ nm}$ value of the mixed probiotic suspension at 0 h; and $A_{mix}$ represents an $OD_{600\ nm}$ value at different time points.

Figure 7:
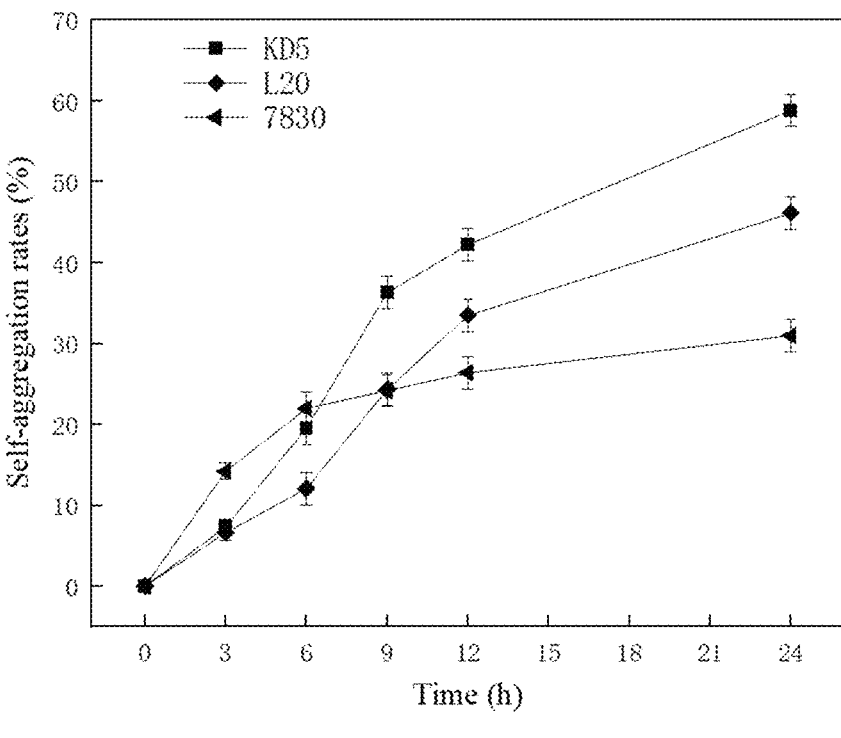
FIG. 7 illustrates a schematic diagram of self-aggregation rates of the *Lacticaseibacillus rhamnosus* KD5, the *Lacti-plantibacillus plantarum* 7830, and the *Lacticaseibacillus rhamnosus* L20.

Self-aggregation refers to the aggregation of cells themselves, thereby protecting the central cells from the influence of harmful substances from the outside world. As shown in FIG. 7, with the extension of time, the self-aggregation rates of the strains show an upward trend. After 24 h, the ranking of the self-aggregation rates is: KD5>L20>7830, ranging from 31% to 58.86%.

In addition to the ability to self-aggregation, probiotics also have the ability to coaggregation with pathogens. This ability allows probiotics to encapsulate pathogens and prevent them from colonizing in the gastrointestinal tract, which helps the health of the human digestive system. The coaggregation rate results of the *Lacticaseibacillus rhamnosus* KD5, the *Lactiplantibacillus* plantarum 7830, and the *Lacticaseibacillus rhamnosus* L20 with pathogenic bacteria are shown in FIGS. 8A-8B.

Figure 8A:
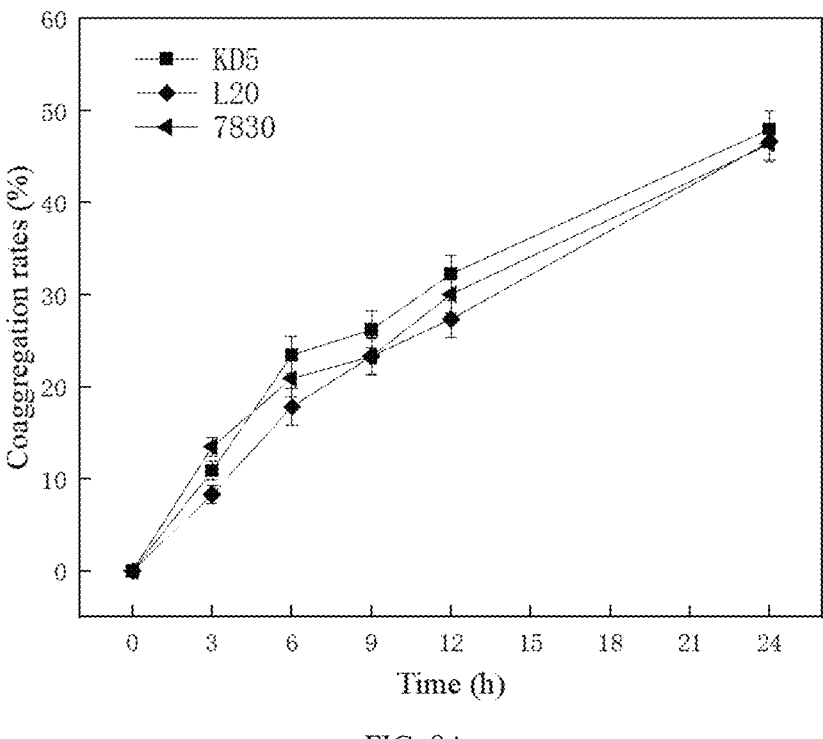
FIG. 8A illustrates a schematic diagram of coaggregation rates of the *Lacticaseibacillus rhamnosus* KD5, the *Lacti-plantibacillus plantarum* 7830, and the *Lacticaseibacillus rhamnosus* L20 with the *Escherichia coli*.
Figure 8B:
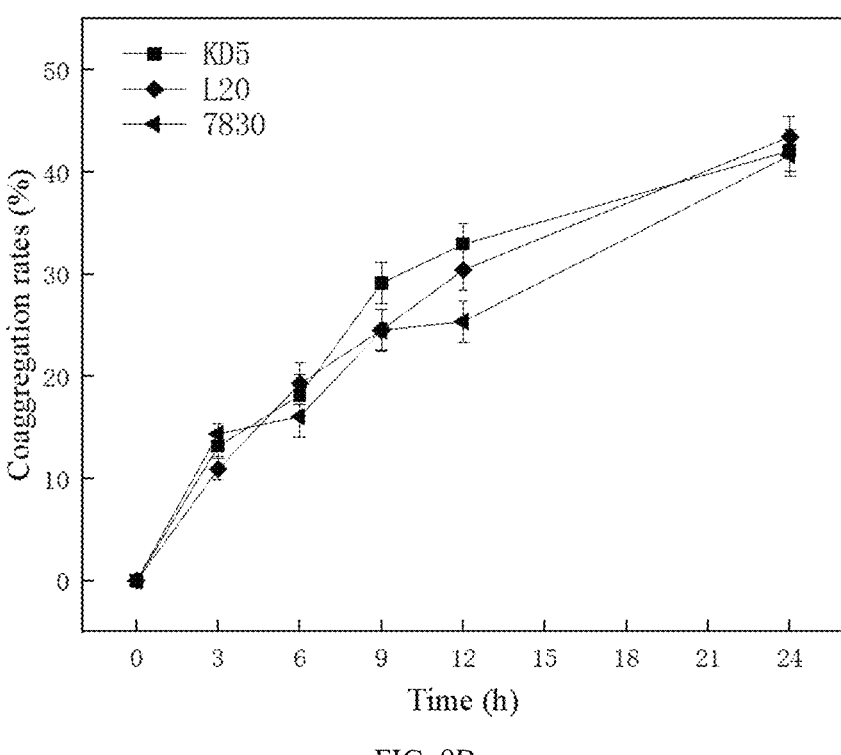
FIG. 8B illustrates a schematic diagram of coaggregation rates of the *Lacticaseibacillus rhamnosus* KD5, the *Lacti-plantibacillus plantarum* 7830, and the *Lacticaseibacillus rhamnosus* L20 with *Staphylococcus aureus*.

It can be seen from FIGS. 8A-8B, the coaggregation rates measured for different pathogens are not much different. For *Staphylococcus aureus* (FIG. 8A), the ranking of the coaggregation rates after 24 h is: KD5>L20>7830, ranging from 46.41% to 48.01%. For *Escherichia coli* (FIG. 8B), the overall trend of the ranking of the coaggregation rates after 24 h is similar to that of *Staphylococcus aureus*, ranging from 41.65% to 43.47%, and the coaggregation rate of the *Lacticaseibacillus rhamnosus* KD5 is 42.12%. Studies have found that probiotics with higher self-aggregation ability also have better coaggregation effects on pathogenic bacteria. This shows that the self-aggregation and coaggregation abilities of the *Lacticaseibacillus rhamnosus* KD5 in the disclosure are strong.

Embodiment 3 Study on the Production of Antihypertensive Peptides by Fermenting Goat Milk with *Lacticaseibacillus rhamnosus* KD5

1. Activity of Antihypertensive Peptides of Goat Milk Fermented with *Lacticaseibacillus rhamnosus* KD5

Lyophilized powder of *Lacticaseibacillus rhamnosus* KD5, *Lactiplantibacillus* plantarum 7830, and *Lacticaseibacillus rhamnosus* L20 are inoculated at an inoculum amount of 0.01% into goat milk sterilized at 95° C. for 10 min and cooled to 37° C., fermented at 37° C. for 22 h, and centrifuged to obtain supernatants. ACE inhibition rates of the supernatants are determined by using an angiotensin converting enzyme inhibitor activity detection kit (BC5575-100T/96S, Beijing Solarbio Technology Co., Ltd., the determination steps are shown in the instruction manual), and the antihypertensive drug captopril (0.25 micromoles per liter abbreviated as μmol/L) is used as a control. The results are shown in FIG. 9.

Figure 9:
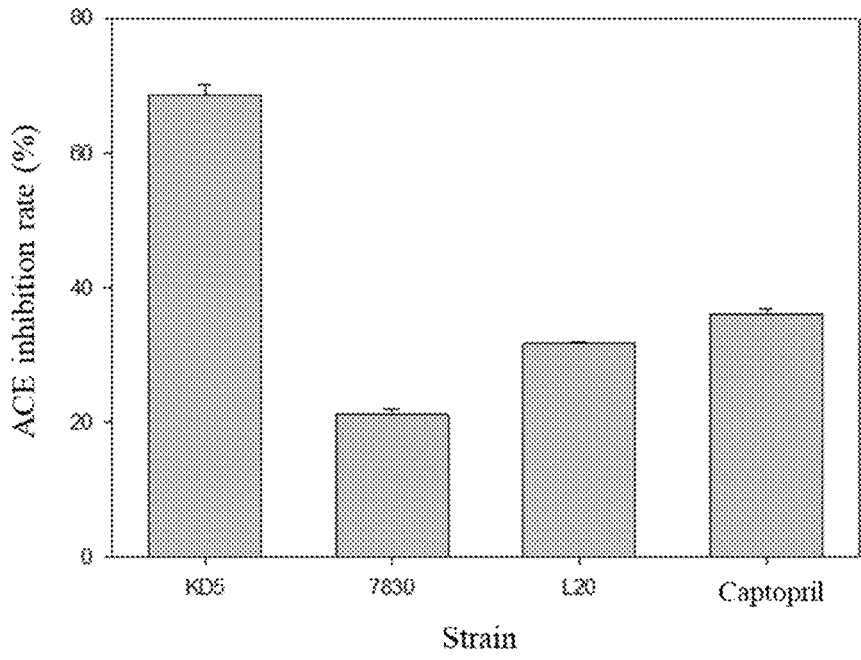
FIG. 9 illustrates a schematic diagram of ACE inhibition rates of fermented goat milk of the *Lacticaseibacillus rham-nosus* KD5, the *Lactiplantibacillus plantarum* 7830, and the *Lacticaseibacillus rhamnosus* L20.

It can be seen from FIG. 9, the fermented milk of the three probiotics all contain antihypertensive peptides. The ACE inhibition rates of the supernatants of the fermented milk of the *Lacticaseibacillus rhamnosus* KD5, the *Lactiplantibacillus* plantarum 7830, and the *Lacticaseibacillus rhamnosus* L20 are 68.56%, 21.04% and 31.63%, respectively. The ACE inhibition rate of 0.25 μmol/L antihypertensive drug captopril is 36.75%. It can be seen that the activity of the antihypertensive peptides in the fermented milk of the *Lacticaseibacillus rhamnosus* KD5 is significantly higher than that of the other two probiotics and 0.25 μmol/L antihypertensive drug captopril.

2. Effects of Fermentation Conditions on the Production of Antihypertensive Peptides by Fermenting Goat Milk with *Lacticaseibacillus rhamnosus* KD5

The lyophilized powder of *Lacticaseibacillus rhamnosus* KD5, as a starter, is inoculated into goat milk, and the effects of inoculation amount (0.01%, 0.02%, 0.03%, 0.04%, and 0.05%, w/v), fermentation temperature (31° C., 34° C., 37° C., 40° C., and 43° C.) and fermentation time (20 h, 22 h, 24 h, 26 h, and 28 h) on the production of antihypertensive peptides by fermenting goat milk with the *Lacticaseibacillus rhamnosus* KD5 are studied, and the ACE inhibition rate and pH of fermented goat milk are determined. The basic experimental conditions are fermentation time of 22 h, fermentation temperature of 37° C., and inoculation amount of 0.01%. The results are shown in FIGS. 10A-10C.

Figure 10A:
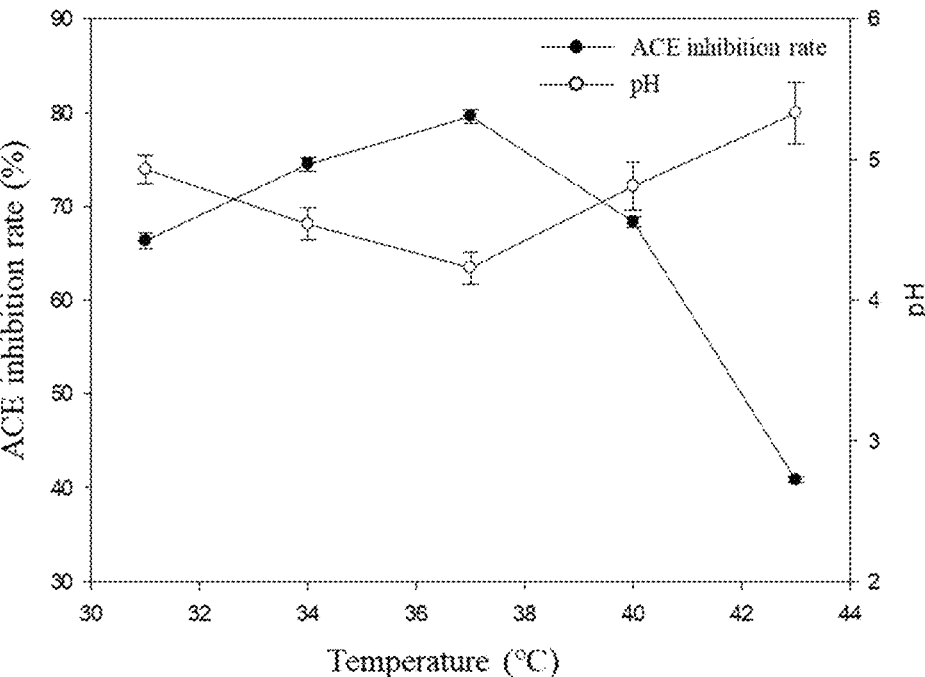
FIG. 10A illustrates a schematic diagram of an effect of temperature on production of antihypertensive peptides by fermenting goat milk with the *Lacticaseibacillus rhamnosus* KD5.
Figure 10B:
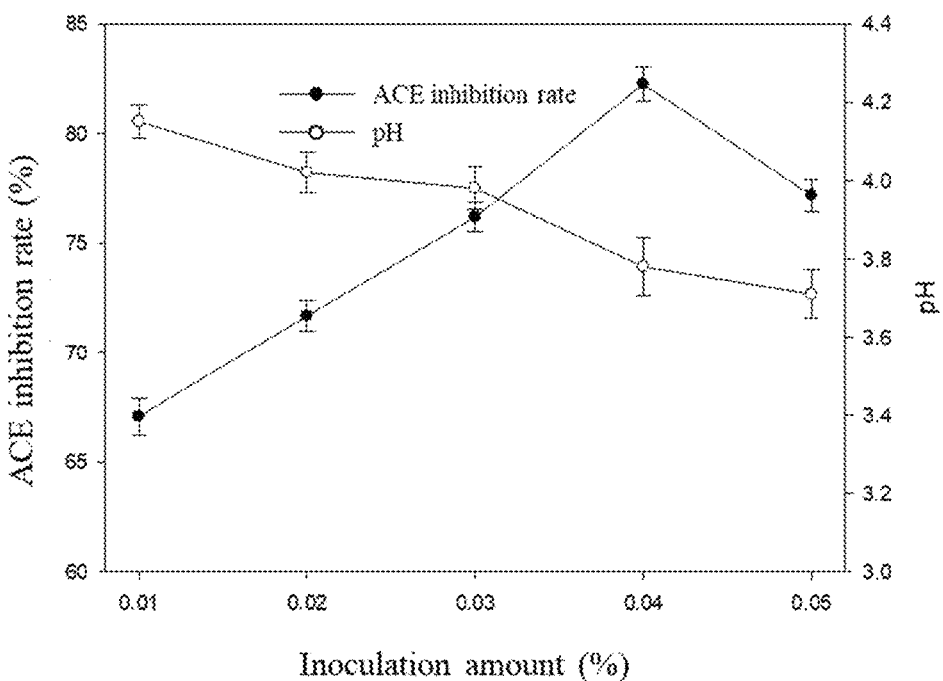
FIG. 10B illustrates a schematic diagram of an effect of inoculation amount on production of antihypertensive pep-tides by fermenting goat milk with the *Lacticaseibacillus rhamnosus* KD5.
Figure 10C:
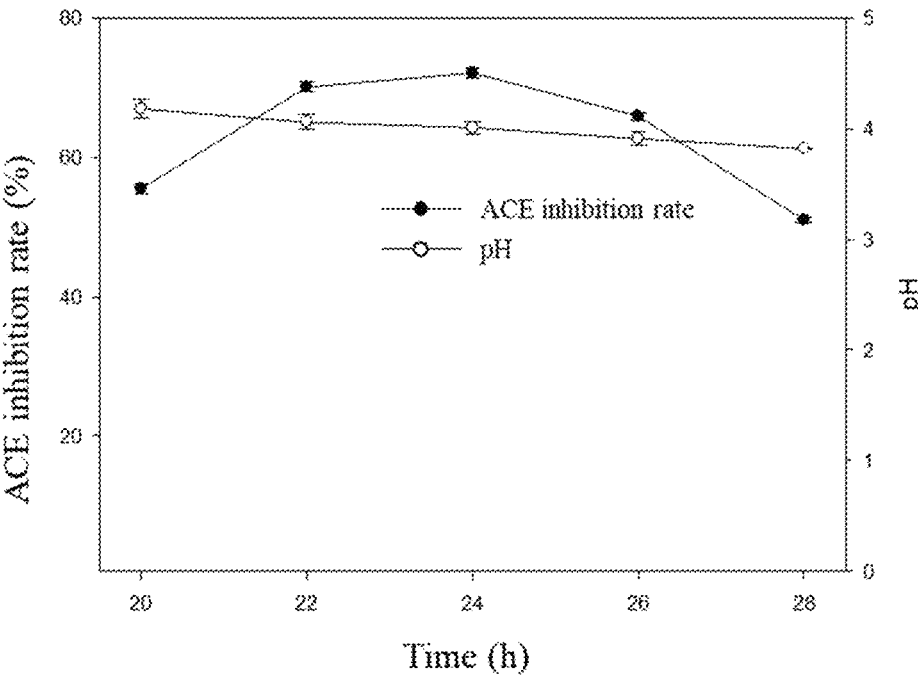
FIG. 10C illustrates a schematic diagram of an effect of fermentation time on production of antihypertensive pep-tides by fermenting goat milk with the *Lacticaseibacillus rhamnosus* KD5.
Figure 11:
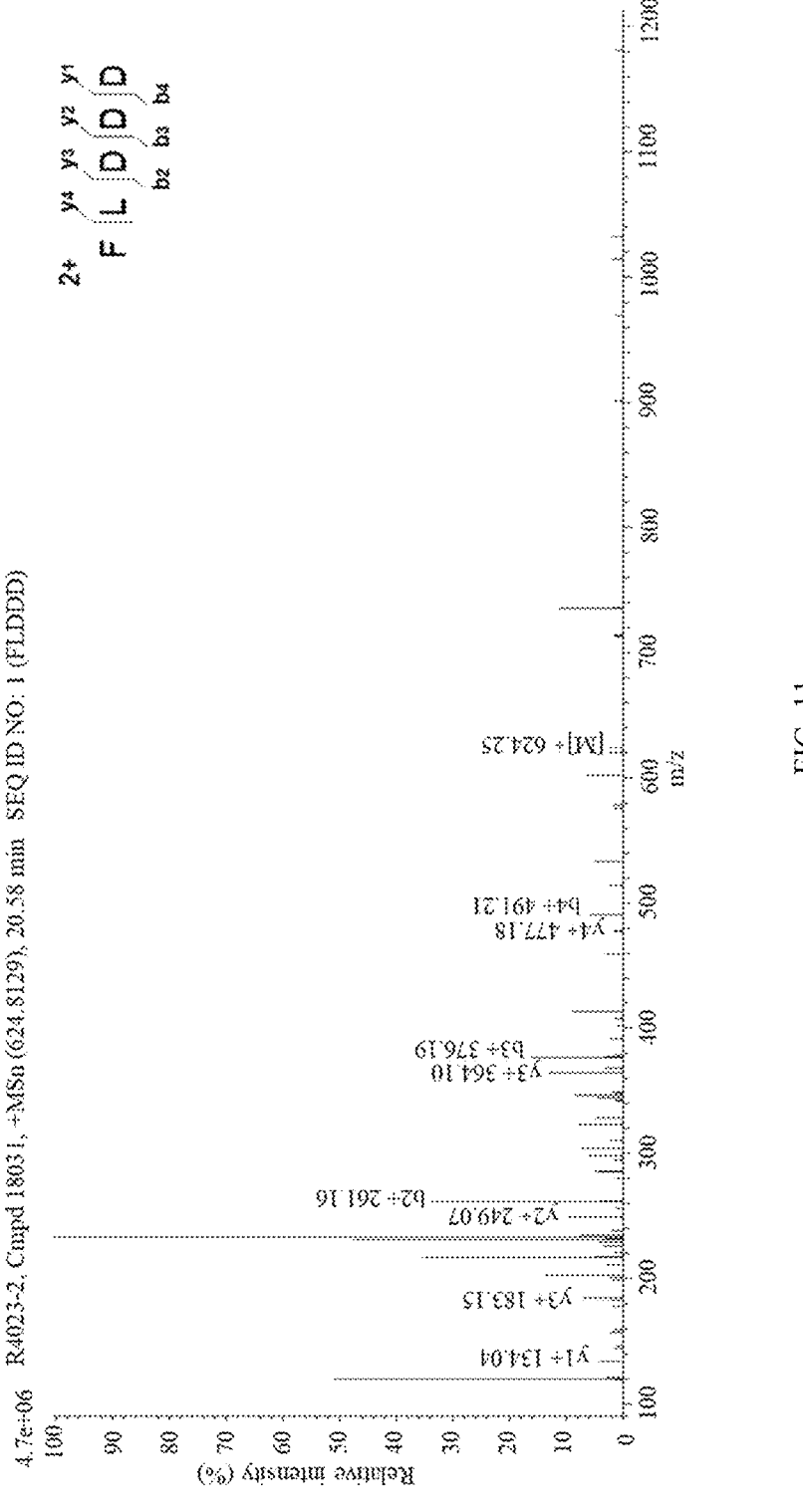
FIGS. 11-26 illustrate secondary mass spectrometry diagrams of 16 peptides in antihypertensive peptide powder.
Figure 12:
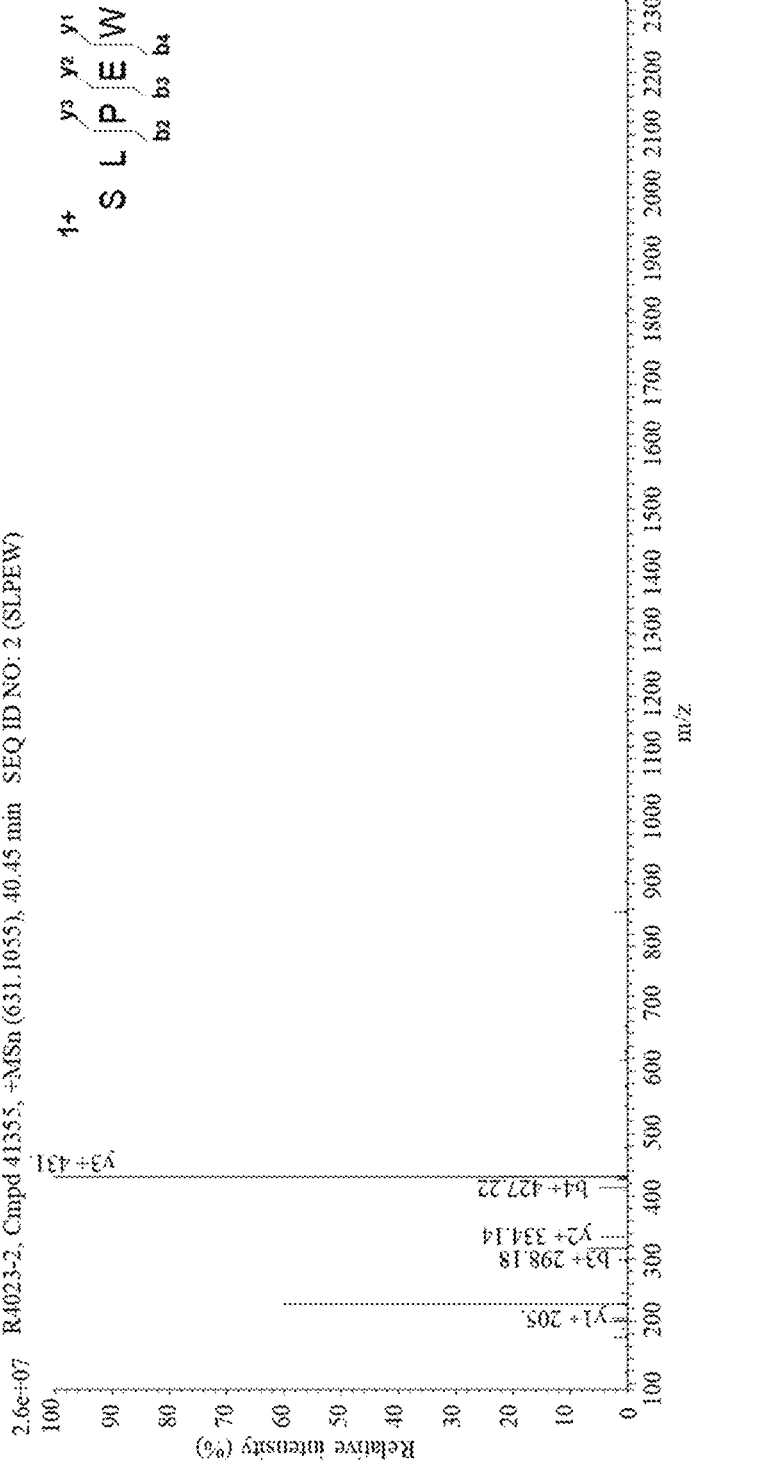
Figure 13:
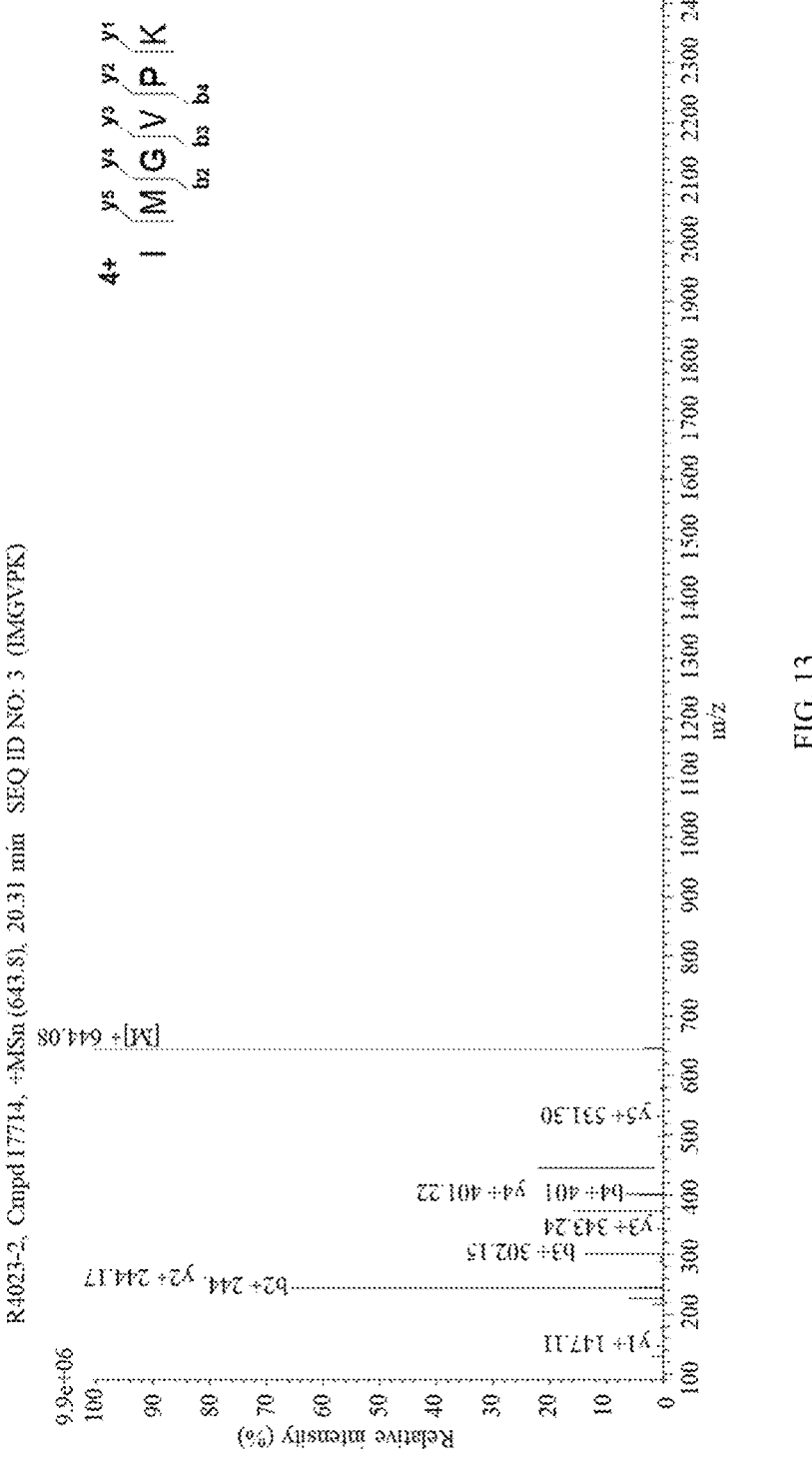
Figure 14:
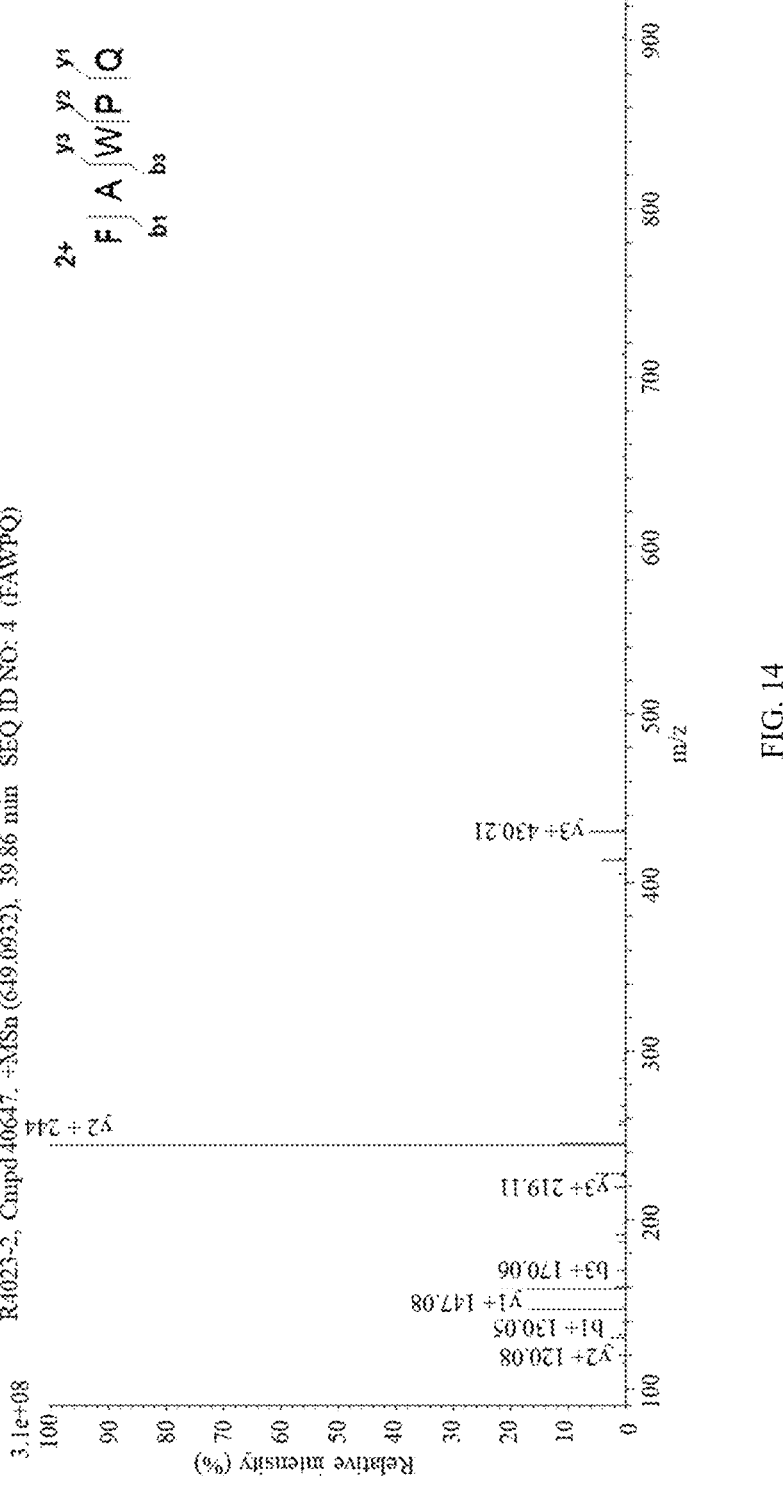
Figure 15:
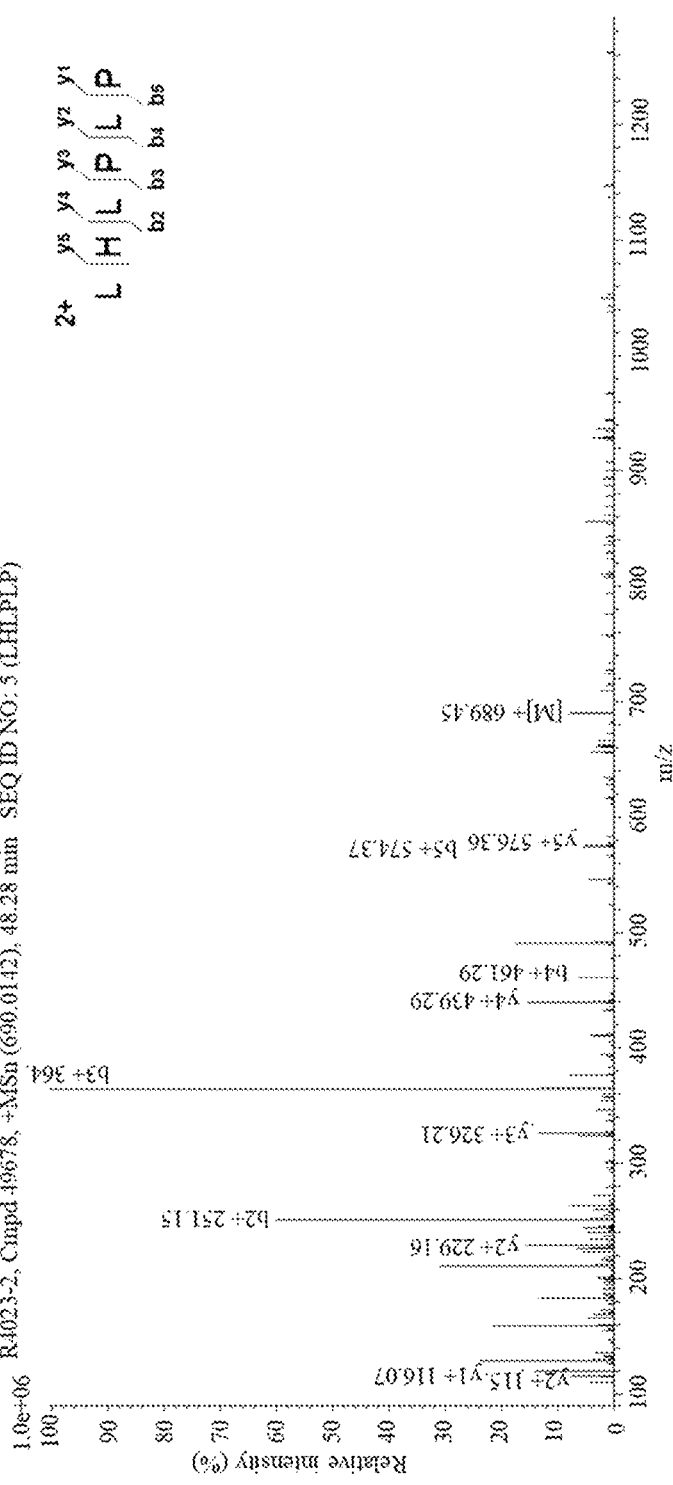
Figure 16:
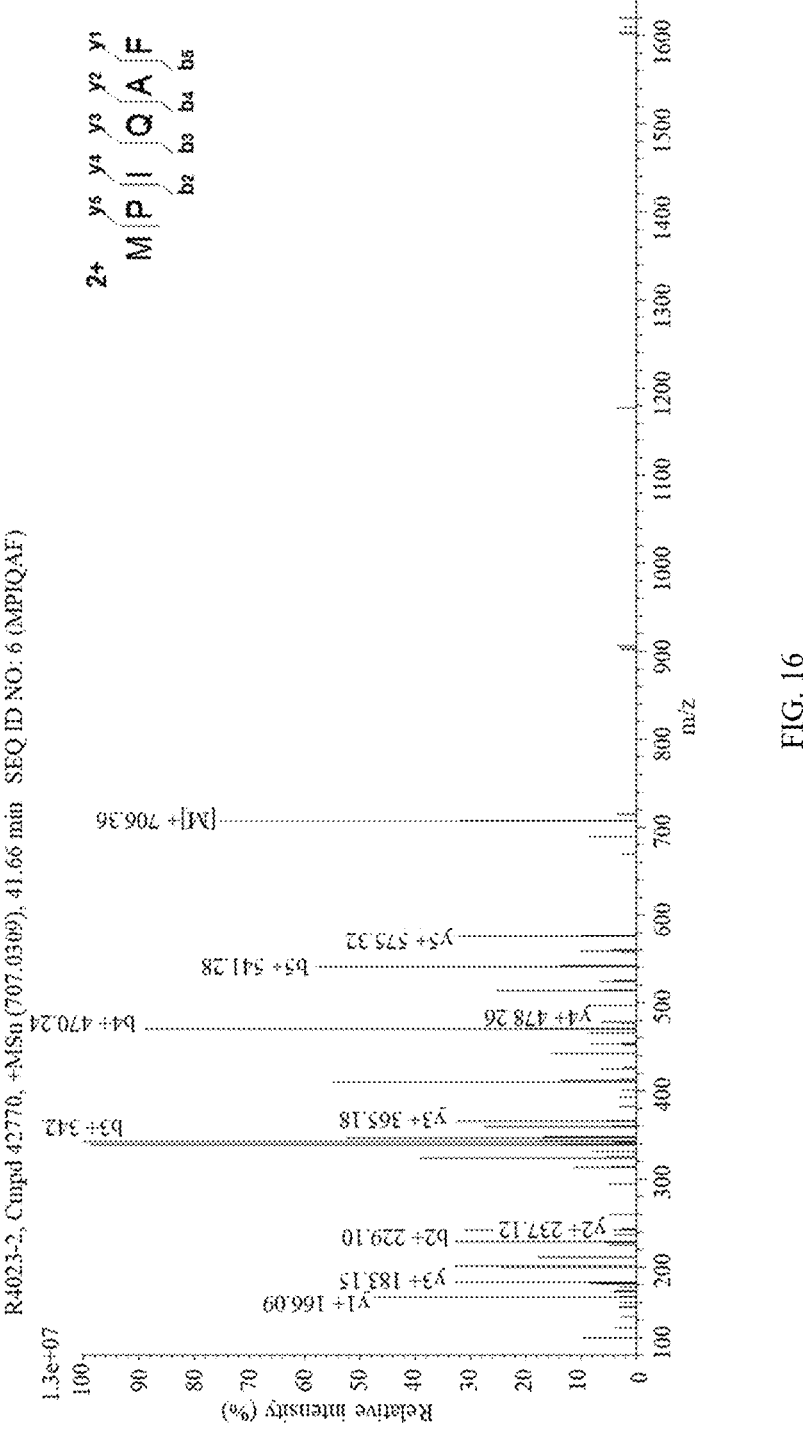
Figure 17:
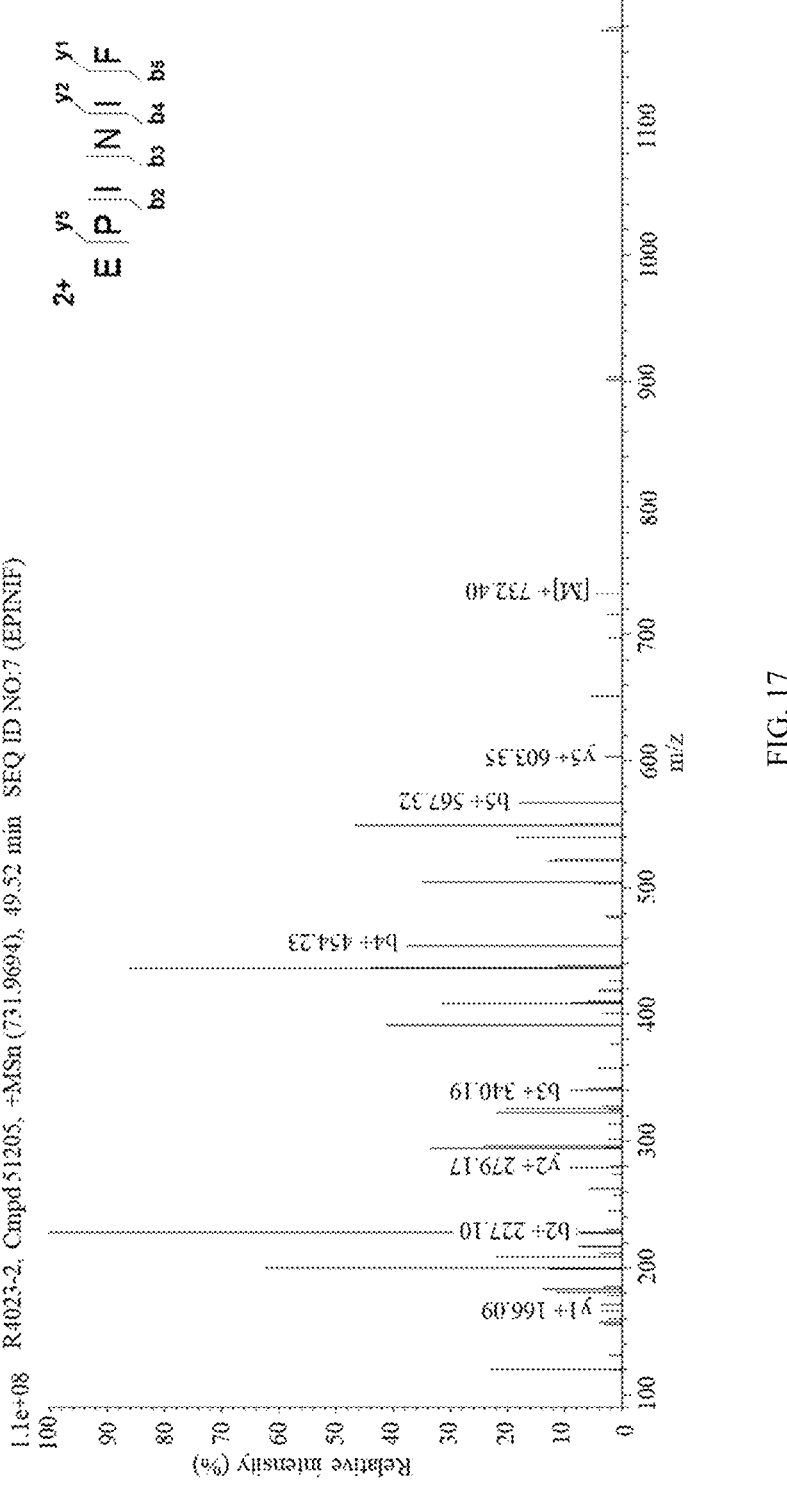
Figure 18:
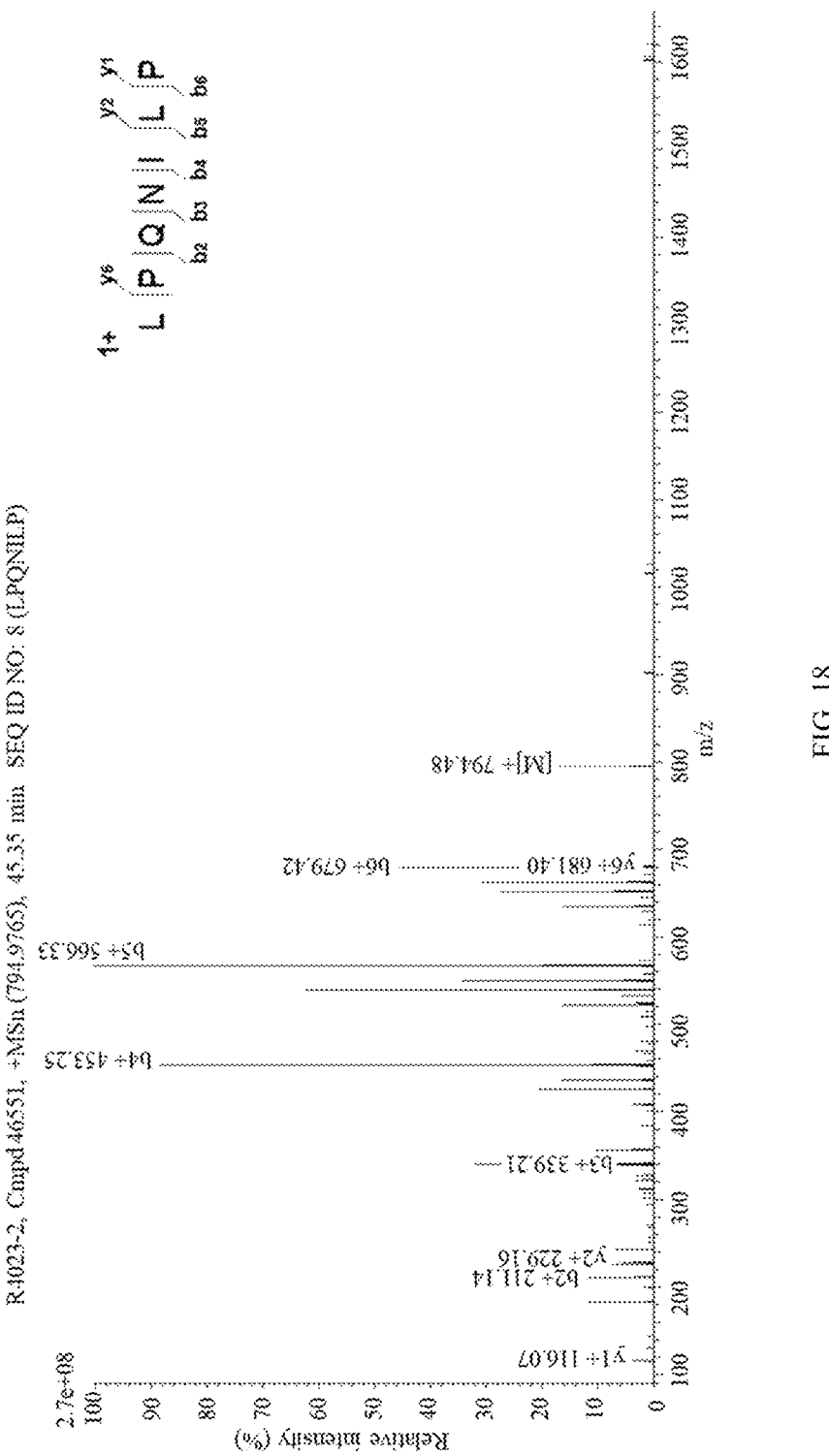
Figure 19:
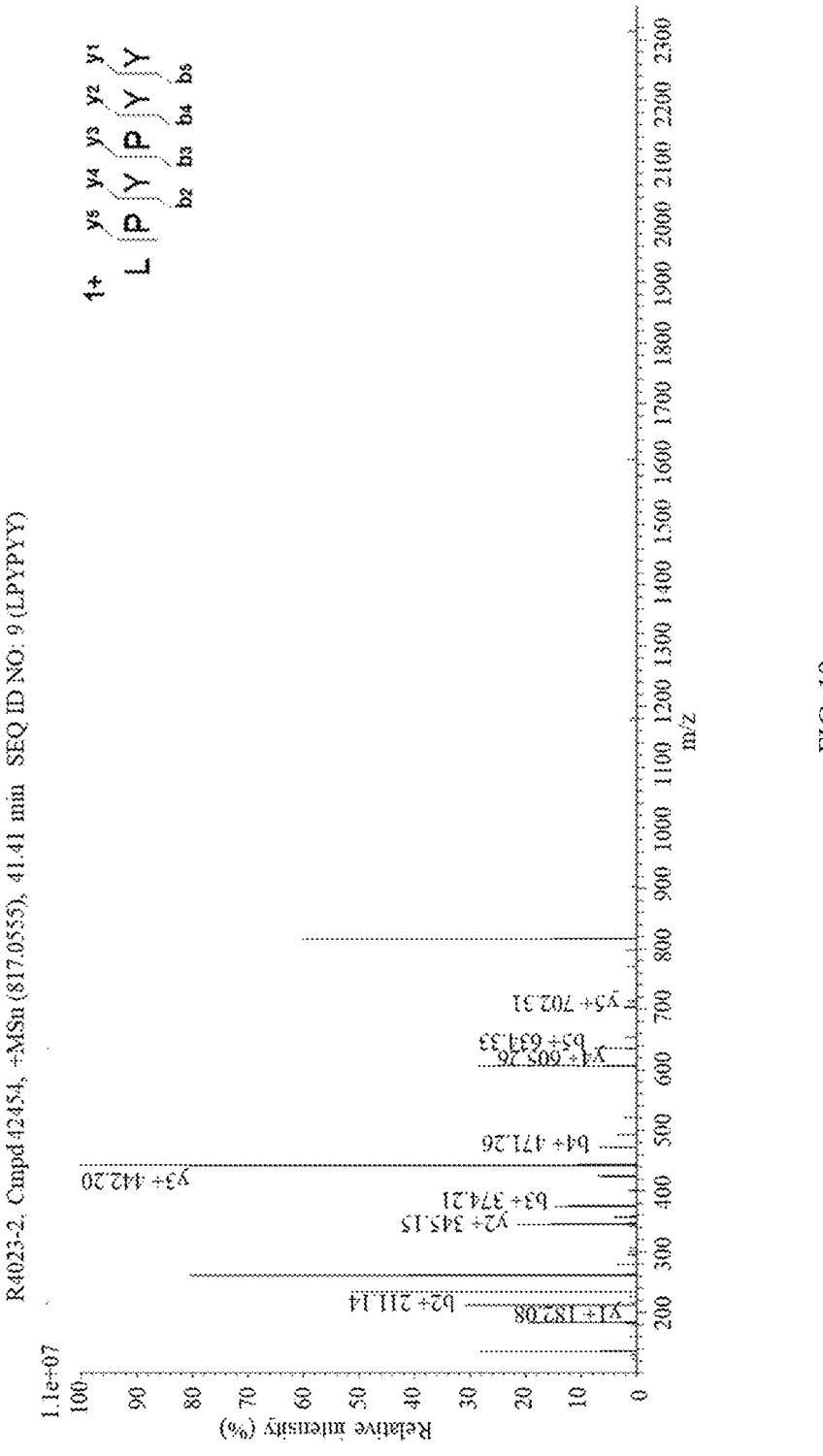
Figure 20:
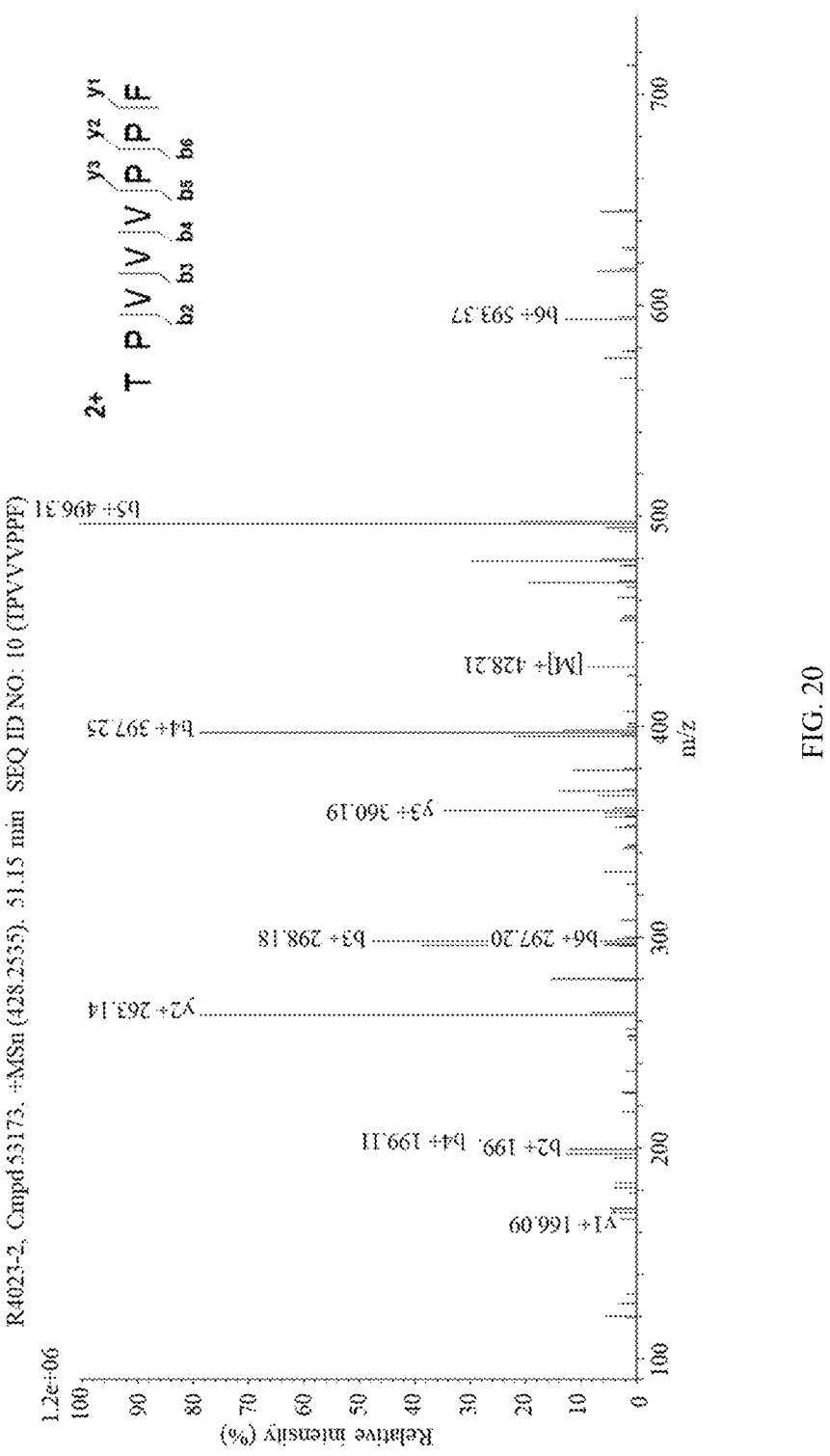
Figure 21:
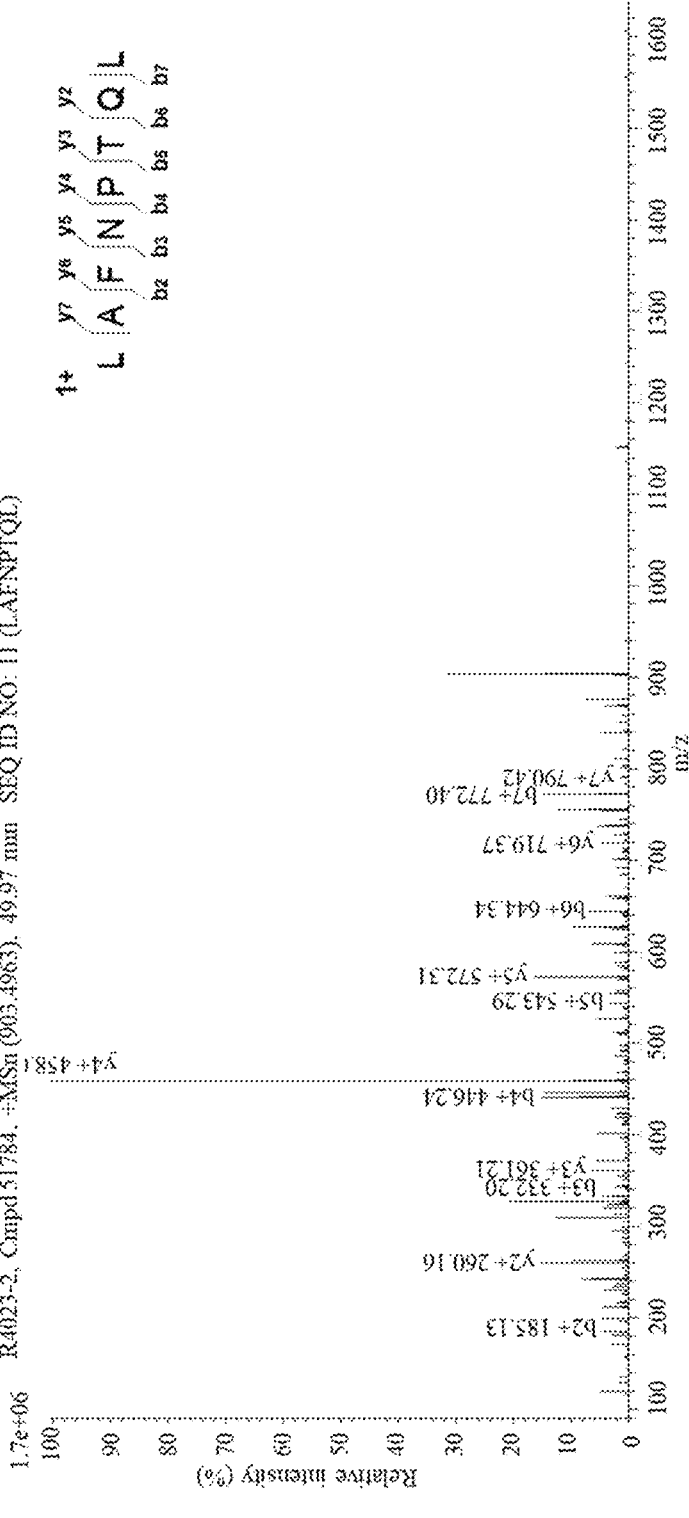
Figure 22:
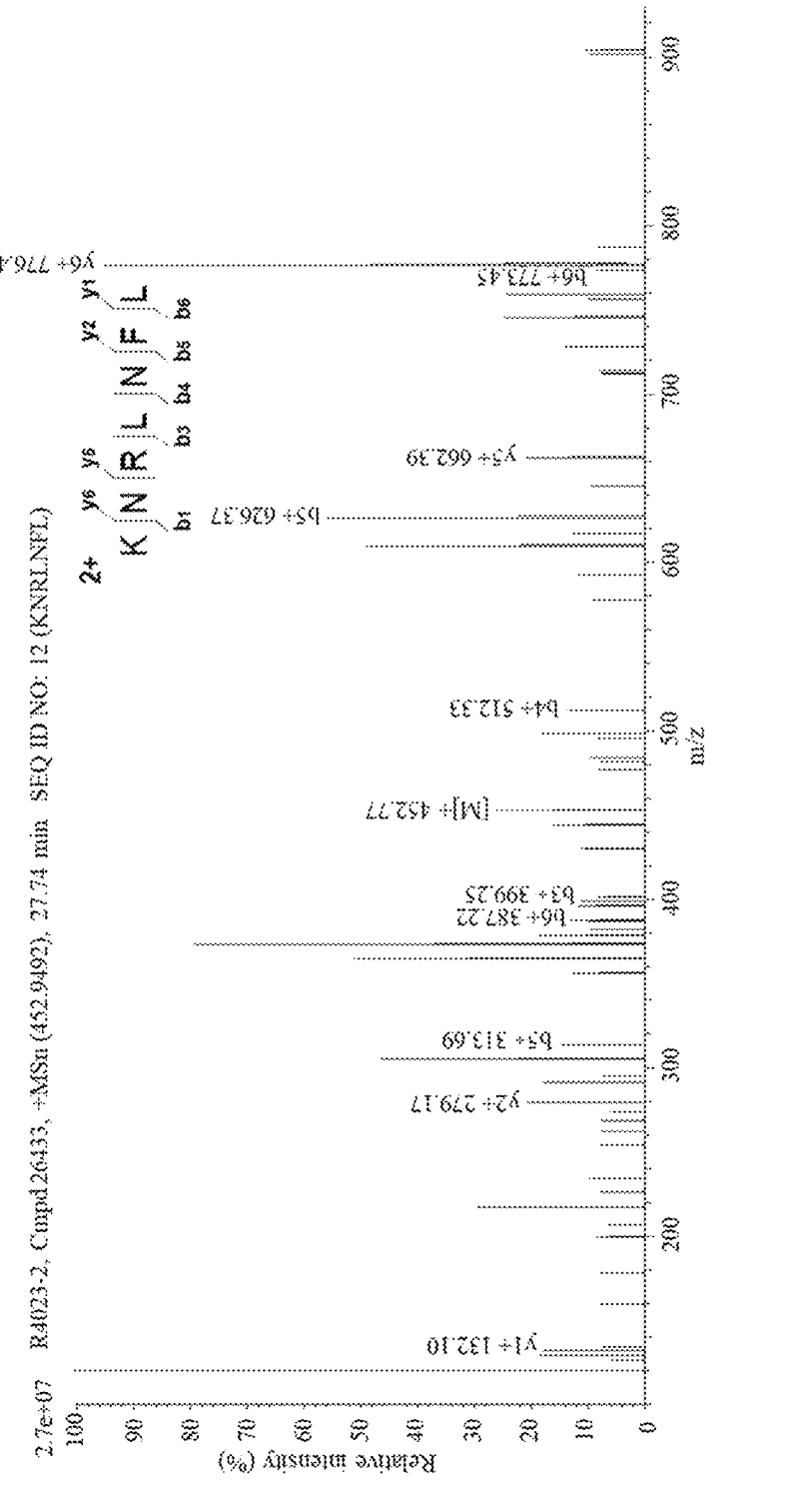
Figure 23:
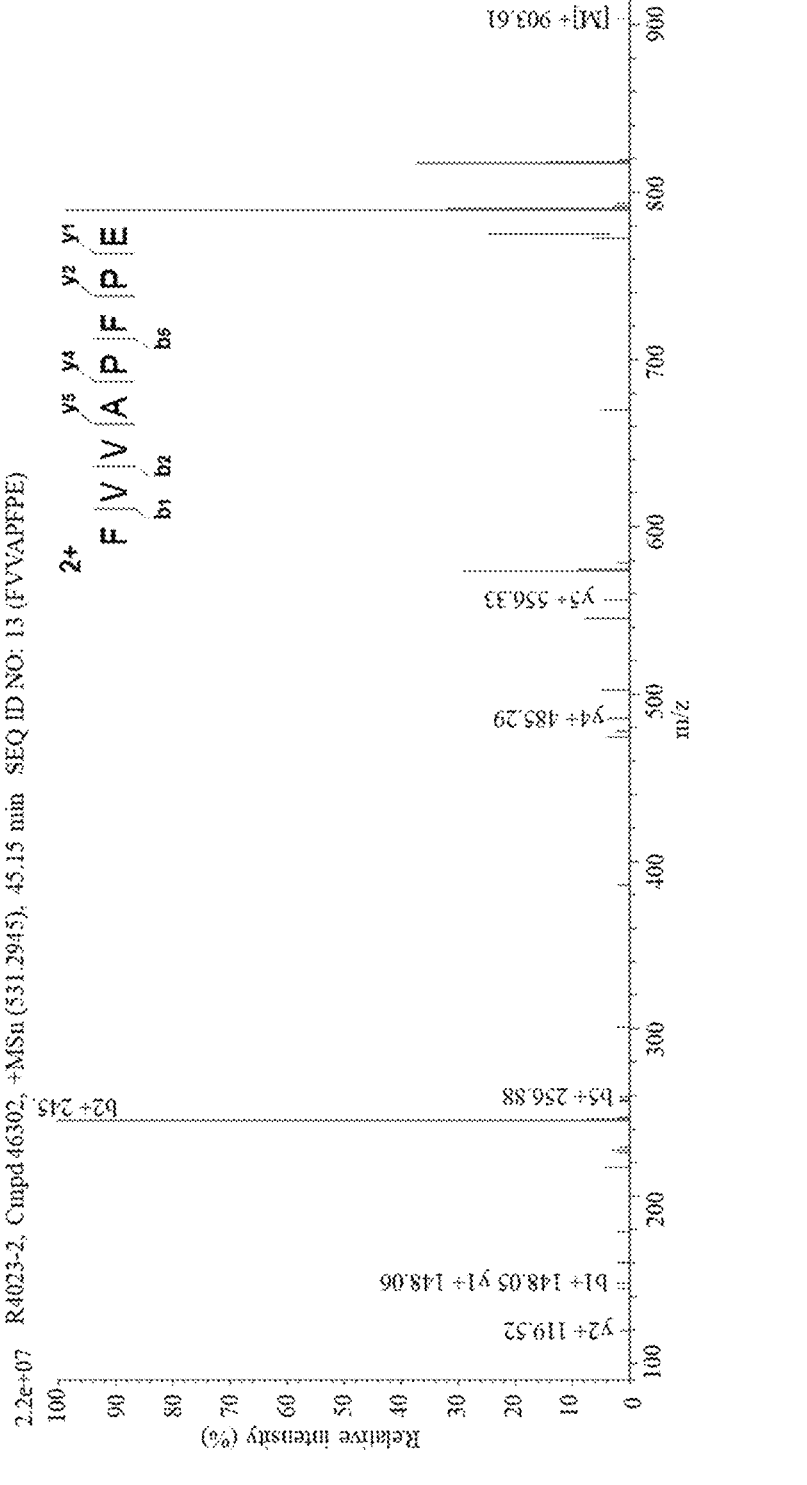
Figure 24:
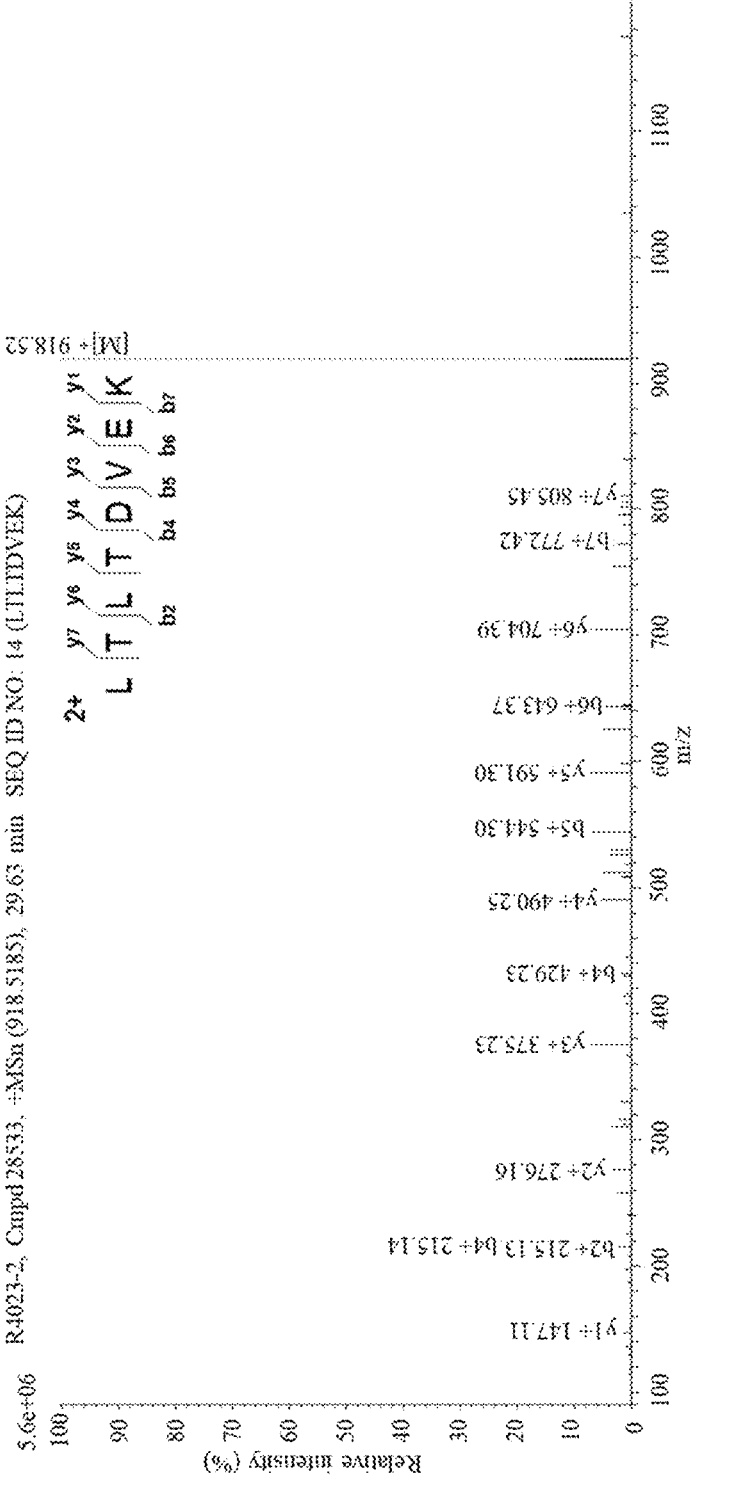
Figure 25:
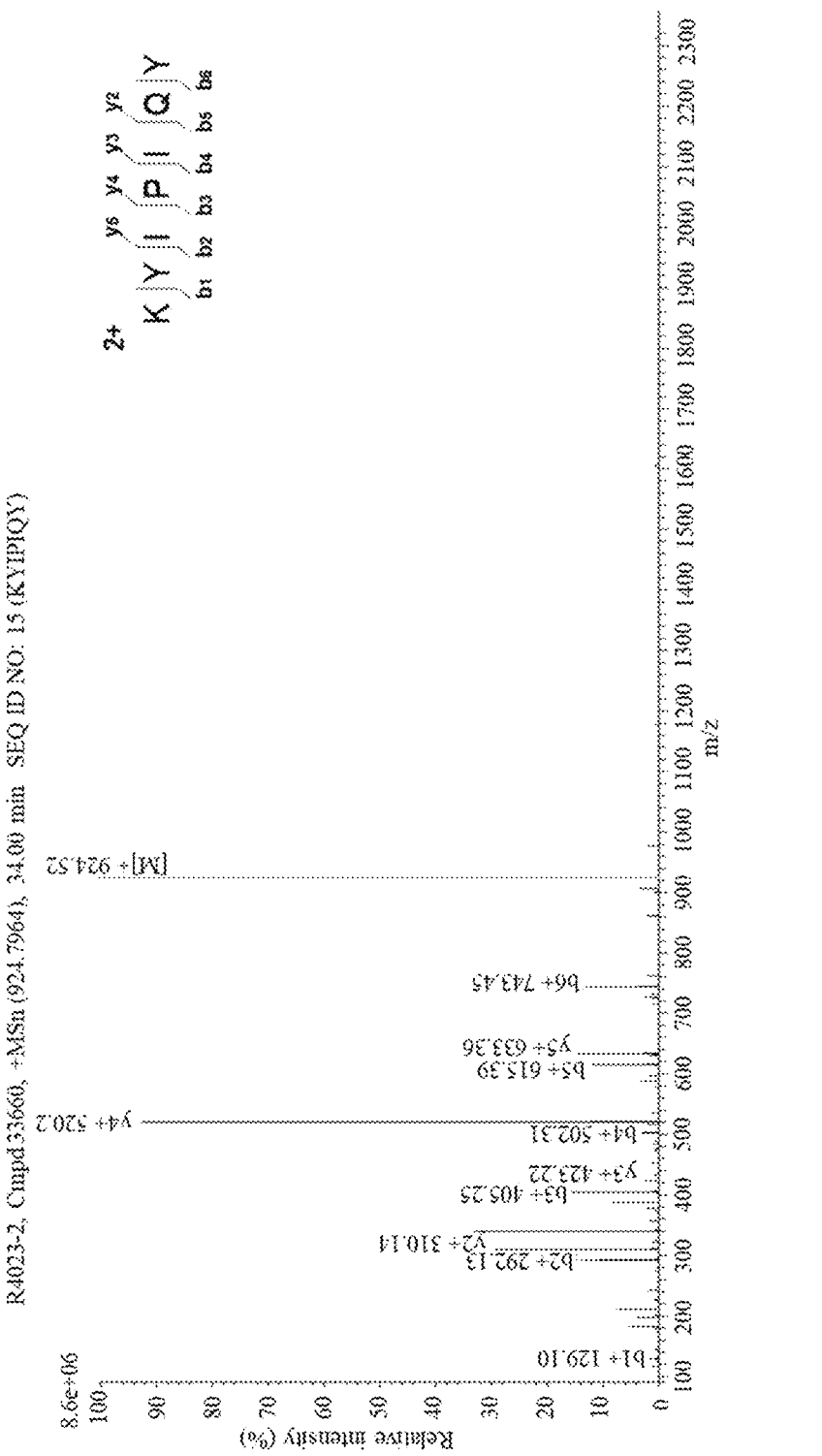
Figure 26:
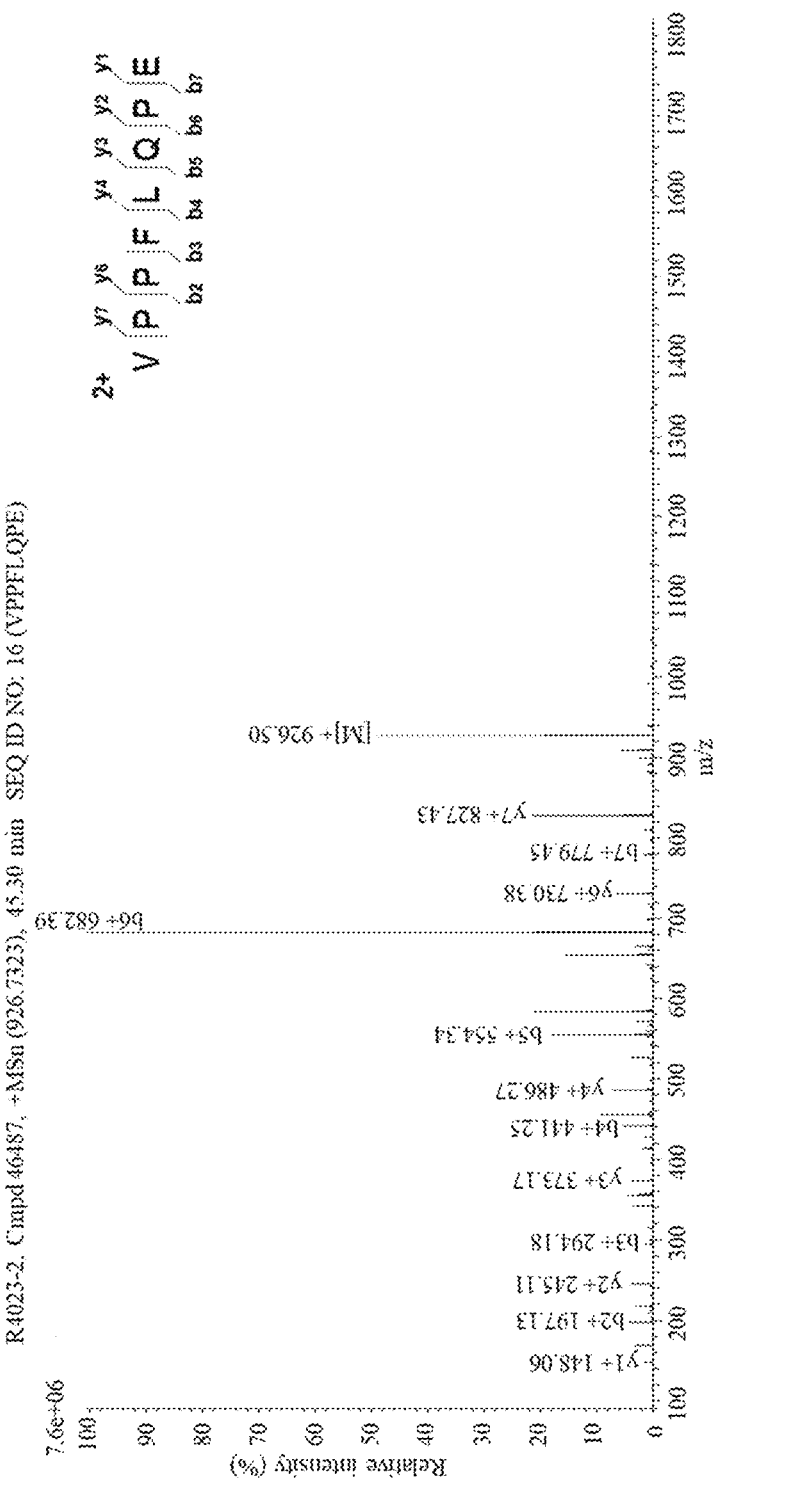

It can be seen from FIGS. 10A-10C, with the increase of fermentation temperature, the ACE inhibition rate in the goat milk fermented by *Lacticaseibacillus rhamnosus* KD5 first increased and then decreased, and the pH first decreased and then increased, showing opposite trends. The ACE inhibition rate is in a range of 40.82% to 79.59%, which is because the increase in temperature is beneficial to *Lacticaseibacillus rhamnosus* KD5, thereby metabolizing and producing more antihypertensive peptides, but when the temperature is too high, the probiotic will age prematurely, resulting in less antihypertensive peptides.

With the increase of inoculum amount, the ACE inhibition rate in the goat milk fermented by *Lacticaseibacillus rhamnosus* KD5 increased first and then decreased, and the pH gradually decreased. This may be because the increase in inoculum amount is conducive to the metabolism and production of more antihypertensive peptides. However, the excessive inoculum amount causes the nutrients in the goat milk to be consumed too quickly, resulting in the decomposition of antihypertensive peptides. The ACE inhibition rate is in a range of 68.06% to 82.25%.

With the extension of fermentation time, the ACE inhibition rate and pH of the goat milk fermented by *Lacticaseibacillus rhamnosus* KD5 gradually decreased, and the ACE inhibition rate is in a range of 51.02% to 72.11%.

With the ACE inhibition rate higher than 65% as the goal, it can be seen that the suitable conditions for fermenting the goat milk with *Lacticaseibacillus rhamnosus* KD5 to produce antihypertensive peptides are: inoculation amount of 0.01%-0.05%, temperature of 31° C. to 40° C., and fermentation time of 22 h to 26 h.

Embodiment 4 Preparation of Antihypertensive Peptides and Peptide Spectrum Identification The antihypertensive peptide probiotic fermented goat milk is centrifuged to obtain whey, and the whey is separated by ultrafiltration to obtain three components (A: >3 k Daltons abbreviated as Da, B: 1-3 k Da and C: <1 k Da). As shown in Table 4, the ACE inhibitory activity of the peptides is closely related to their relative molecular mass, and the ACE inhibition rate increases with the decrease of molecular weight. The antihypertensive peptide of component C has the best activity, with an ACE inhibition rate of 85.9%. The above results show that the activity of the component with 1 k Da peptides is improved after ultrafiltration, and it has a strong ACE inhibitory activity, indicating that the antihypertensive peptides are mainly concentrated in the C component.

TABLE 2

Antihypertensive peptide activity of each ultrafiltration component

| Component | ACE inhibition rate (%) |
|---|---|
| Whey | 83.1 ± 1.15 |
| A | 31.2 ± 0.89 |
| B | 50.7 ± 1.28 |
| C | 85.9 ± 1.06 |

The C component is further purified by dextran gel (such as Sephadex G-15), and the ACE inhibition rates of different components are compared. The component with the highest ACE inhibition rate is identified by high-performance liquid chromatography-tandem mass spectrometry (HPLC-MS/MS), and 16 peptides are obtained (Table 3).

TABLE 3

Amino acid sequences of antihypertensive peptides

| Serial Number | Peptide sequence | Number of amino acids | Molecular weight (Da) | Origin and location of lactoprotein |
|---|---|---|---|---|
| 1 | FLDDD (SEQ ID NO: 1) | 5 | 623.24 | α-lactalbumin f (99-103) |
| 2 | SLPEW (SEQ ID NO: 2) | 5 | 630.30 | Lactoferrin f (31-35) |
| 3 | IMGVPK (SEQ ID NO: 3) | 6 | 643.37 | β-casein f (107-112) |
| 4 | FAWPQ (SEQ ID NO: 4) | 5 | 647.31 | αs$_2$-casein (190-194) |
| 5 | LHLPLP (SEQ ID NO: 5) | 6 | 688.43 | β-casein f (148-153) |
| 6 | MPIQAF (SEQ ID NO: 6) | 6 | 705.35 | β-casein f (198-203) |
| 7 | EPINIF (SEQ ID NO: 7) | 6 | 731.39 | αs$_2$-casein f (27-32) |
| 8 | LPQNILP (SEQ ID NO: 8) | 7 | 793.47 | β-casein f (85-91) |
| 9 | LPYPYY (SEQ ID NO: 9) | 6 | 814.39 | κ-casein f (77-82) |

13

TABLE 3-continued

Amino acid sequences
of antihypertensive peptides

| Serial Number | Peptide sequence | Number of amino acids | Molecular weight (Da) | Origin and location of lactoprotein |
|---|---|---|---|---|
| 10 | TPVVVPPF (SEQ ID NO: 10) | 8 | 854.49 | β-casein f (95-102) |
| 11 | LAFNPTQL (SEQ ID NO: 11) | 8 | 902.49 | β-lactoglobulin f (27-32) |
| 12 | KNRLNFL (SEQ ID NO: 12) | 7 | 903.53 | αs₂-casein (174-180) |
| 13 | FVVAPFPE (SEQ ID NO: 13) | 8 | 904.47 | αs₁-casein (38-45) |
| 14 | LTLTDVEK (SEQ ID NO: 14) | 8 | 917.51 | β-casein f (140-147) |
| 15 | KYIPIQY (SEQ ID NO: 15) | 7 | 923.51 | κ-casein f (45-51) |
| 16 | VPPFLQPE (SEQ ID NO: 16) | 8 | 925.49 | β-casein f (99-106) |

It can be seen from Table 3, the number of amino acids in the 16 peptides in the antihypertensive peptide powder is in a range of 5 to 8, and the molecular weight is in a range of 623.24 Da to 903.53 Da. They come from β-casein, αs₁ and αs₂-casein, κ-casein, α-lactalbumin, β-lactoglobulin and lactoferrin from goat milk.

The secondary mass spectrometry diagrams of various goat milk antihypertensive peptides are shown in FIGS. 11 to 26.

Embodiment 5 Preparation of Antihypertensive Peptide Probiotic Goat Milk Powder The antihypertensive peptide probiotic fermented goat milk is subjected to high-temperature spray-drying (small spray dryer, YM-6000Y, Shanghai Yuming Instrument Co., Ltd.) and vacuum low-temperature spray-drying (vacuum low-temperature spray dryer, BILON-VSD1500, Bilon Company), respectively. The high-temperature spray-drying conditions are an inlet air temperature of 170° C. and an outlet air temperature of 85° C. The vacuum low-temperature spray-drying conditions are 65° C., 70° C. and 75° C., respectively, and the drying negative pressure is 0.03 MPa to 0.04 MPa. Samples are taken to determine the viable count before and after spray-drying, the survival rate and the viable count of probiotics are calculated, and the ACE inhibitory activity (IC₅₀ value) of the antihypertensive peptide probiotic goat milk powder is determined. The results are shown in Table 4.

TABLE 4

Effects of high-temperature spray-drying and vacuum low-temperature spray-drying on the viable count of probiotics and the activity of antihypertensive peptides

| Index | High-temperature spray-drying | Vacuum low-temperature spray-drying | | |
|---|---|---|---|---|
| | | 65° C. | 70° C. | 75° C. |
| Viable count/10⁸ CFU/g | 0.75 | 6.94 | 5.68 | 4.41 |
| Survival rate/% | 9.01 | 83.58 | 68.49 | 53.19 |
| ACE inhibitory activity IC₅₀ (g/mL) | 0.109 | 0.055 | 0.064 | 0.084 |

It can be seen from Table 4, the viable count of probiotics in the antihypertensive peptide probiotic goat milk powder prepared by vacuum low-temperature spray-drying is in a range of 4.41×10⁸ CFU/g to 6.94×10⁸ CFU/g, the survival rate of the probiotics is in a range of 53.19% to 83.58%, and the ACE inhibitory activity IC₅₀ is in a range of 0.055 g/mL to 0.084 g/mL. The viable count and the survival rate are significantly higher than that of the antihypertensive peptide probiotic goat milk powder obtained by high-temperature spray-drying, and the ACE inhibitory activity IC₅₀ is significantly lower than that of the antihypertensive peptide probiotic goat milk powder prepared by high-temperature spray-drying. The smaller the ACE inhibitory activity IC₅₀ value, the stronger the antihypertensive peptide activity, and the lower concentration can inhibit the ACE enzyme activity by 50%. It can be seen that vacuum low-temperature spray-drying is effective in improving the survival rate, viable count and ACE inhibitory activity of probiotics.

In summary, the disclosure provides an antihypertensive peptide probiotic goat milk powder and a preparation method thereof. Goat milk is used as a raw material, the goat milk is sterilized and then cooled, and the screened probiotic bacteria for fermenting goat milk to produce antihypertensive peptides, namely *Lacticaseibacillus rhamnosus* KD5, is added and stirred evenly, and then fermented at a constant temperature. After the fermentation is completed, probiotic fermented goat milk containing antihypertensive peptides is obtained. After mixing the probiotic fermented goat milk evenly with or without nutritional fortifiers for middle-aged and elderly people, it is subjected to vacuum low-temperature spray-drying to obtain antihypertensive peptide probiotic goat milk powder, which has a high ACE inhibition rate and can be used to assist consumers in lowering blood pressure.

SEQUENCE LISTING

```
Sequence total quantity: 16
SEQ ID NO: 1              moltype = AA  length = 5
FEATURE                  Location/Qualifiers
source                   1..5
                         mol_type = protein
                         organism = synthetic construct
SEQUENCE: 1
FLDDD                                                      5
```

-continued

```
SEQ ID NO: 2            moltype = AA   length = 5
FEATURE                 Location/Qualifiers
source                  1..5
                        mol_type = protein
                        organism = synthetic construct
SEQUENCE: 2
SLPEW                                                              5

SEQ ID NO: 3            moltype = AA   length = 6
FEATURE                 Location/Qualifiers
source                  1..6
                        mol_type = protein
                        organism = synthetic construct
SEQUENCE: 3
IMGVPK                                                             6

SEQ ID NO: 4            moltype = AA   length = 5
FEATURE                 Location/Qualifiers
source                  1..5
                        mol_type = protein
                        organism = synthetic construct
SEQUENCE: 4
FAWPQ                                                              5

SEQ ID NO: 5            moltype = AA   length = 6
FEATURE                 Location/Qualifiers
source                  1..6
                        mol_type = protein
                        organism = synthetic construct
SEQUENCE: 5
LHLPLP                                                             6

SEQ ID NO: 6            moltype = AA   length = 6
FEATURE                 Location/Qualifiers
source                  1..6
                        mol_type = protein
                        organism = synthetic construct
SEQUENCE: 6
MPIQAF                                                             6

SEQ ID NO: 7            moltype = AA   length = 6
FEATURE                 Location/Qualifiers
source                  1..6
                        mol_type = protein
                        organism = synthetic construct
SEQUENCE: 7
EPINIF                                                             6

SEQ ID NO: 8            moltype = AA   length = 7
FEATURE                 Location/Qualifiers
source                  1..7
                        mol_type = protein
                        organism = synthetic construct
SEQUENCE: 8
LPQNILP                                                           7

SEQ ID NO: 9            moltype = AA   length = 6
FEATURE                 Location/Qualifiers
source                  1..6
                        mol_type = protein
                        organism = synthetic construct
SEQUENCE: 9
LPYPYY                                                            6

SEQ ID NO: 10           moltype = AA   length = 8
FEATURE                 Location/Qualifiers
source                  1..8
                        mol_type = protein
                        organism = synthetic construct
SEQUENCE: 10
TPVVVPPF                                                          8

SEQ ID NO: 11           moltype = AA   length = 8
FEATURE                 Location/Qualifiers
source                  1..8
                        mol_type = protein
                        organism = synthetic construct
SEQUENCE: 11
LAFNPTQL                                                          8
```

-continued

```
SEQ ID NO: 12          moltype = AA  length = 7
FEATURE                Location/Qualifiers
source                 1..7
                       mol_type = protein
                       organism = synthetic construct
SEQUENCE: 12
KNRLNFL                                                          7

SEQ ID NO: 13          moltype = AA  length = 8
FEATURE                Location/Qualifiers
source                 1..8
                       mol_type = protein
                       organism = synthetic construct
SEQUENCE: 13
FVVAPFPE                                                         8

SEQ ID NO: 14          moltype = AA  length = 8
FEATURE                Location/Qualifiers
source                 1..8
                       mol_type = protein
                       organism = synthetic construct
SEQUENCE: 14
LTLTDVEK                                                         8

SEQ ID NO: 15          moltype = AA  length = 7
FEATURE                Location/Qualifiers
source                 1..7
                       mol_type = protein
                       organism = synthetic construct
SEQUENCE: 15
KYIPIQY                                                          7

SEQ ID NO: 16          moltype = AA  length = 8
FEATURE                Location/Qualifiers
source                 1..8
                       mol_type = protein
                       organism = synthetic construct
SEQUENCE: 16
VPPFLQPE                                                         8
```

What is claimed is:

1. A method of making an antihypertensive probiotic dairy product, comprising:

(1) inoculating 0.01% to 0.05% of lyophilized powder of *Lacticaseibacillus rhamnosus* KD5 into sterilized and cooled goat milk to obtain a mixture; and (2) fermenting the mixture at a constant temperature of 34° C. to 40° C. for 22 to 26 hours, wherein the *Lacticaseibacillus rhamnosus* KD5 is preserved at China Center for Type Culture Collection (CCTCC) with a preservation number of CCTCC NO: M20231641, and the antihypertensive probiotic dairy product comprises 16 peptides of amino acid sequences SEQ ID NO: 1-16.

\* \* \* \* \*